United States Patent
Galm et al.

(10) Patent No.: US 10,966,647 B2
(45) Date of Patent: Apr. 6, 2021

(54) DROWSINESS DETECTION

(71) Applicant: Garmin Switzerland GmbH, Schaffhausen (CH)

(72) Inventors: Norbert Galm, Zorneding (DE); Robert G. Mayster, Würzburg (DE); Manuel F. Fehler, Würzburg (DE)

(73) Assignee: Garmin Switzerland GmbH

( * ) Notice: Subject to any disclaimer, the term of this patent is extended or adjusted under 35 U.S.C. 154(b) by 67 days.

(21) Appl. No.: 16/255,474

(22) Filed: Jan. 23, 2019

(65) Prior Publication Data
US 2019/0223773 A1 Jul. 25, 2019

Related U.S. Application Data

(60) Provisional application No. 62/716,464, filed on Aug. 9, 2018, provisional application No. 62/620,804, filed on Jan. 23, 2018.

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0002* (2013.01); *A61B 5/0205* (2013.01); *A61B 5/18* (2013.01);
(Continued)

(58) Field of Classification Search
CPC ..... A61B 5/165; A61B 5/0002; A61B 5/0205; A61B 5/7257; A61B 5/18; A61B 5/681;
(Continued)

(56) References Cited

U.S. PATENT DOCUMENTS 8,306,610 B2 * 11/2012 Mirow ................... G16H 10/20
600/509
9,307,917 B2 4/2016 Hong et al.
(Continued)

FOREIGN PATENT DOCUMENTS

WO 2008/054460 A2 5/2008
WO WO-2017086991 A1 * 5/2017 ........... G06Q 10/107

OTHER PUBLICATIONS

Vicente, J., et al., "Drowsiness Detection Using Heart Rate Variability," Abstract, NCBI, Resources, PubMed.gov, US National Library of Medicine, National Institute of Health, https://www.ncbi.nlm.nih.gov/pubmed/26780463, Med Biol Eng Comput. Jun. 2016;54(6):927-37. doi: 10.1007/s11517-015-1448-7. EPub, Jan. 16, 2016.

(Continued)

*Primary Examiner* — Nathan J Jenness
*Assistant Examiner* — Sebastian X Lukjan
(74) *Attorney, Agent, or Firm* — Samuel M. Korte; Max M. Ali

(57) ABSTRACT

A mobile electronic device is operable to detect and display a mental state of a user such as drowsiness. The mobile electronic device includes a heartrate sensor, a processor, and a display. The heartrate sensor is operable to provide a heartbeat signal indicative of a heartbeat of the user. The processor is operable to: acquire a beat-to-beat interval based upon the heartbeat signal and determine a drowsiness level of the user based at least in part upon the beat-to-beat interval. The display is operable to display an indication of the drowsiness level.

10 Claims, 14 Drawing Sheets

(51) Int. Cl.
*A61B 5/18* (2006.01)
*A61B 5/0205* (2006.01)
*A61B 5/021* (2006.01)
*A61B 5/024* (2006.01)
*A61B 5/11* (2006.01)

(52) U.S. Cl.
CPC ............ *A61B 5/681* (2013.01); *A61B 5/7257* (2013.01); *A61B 5/7275* (2013.01); *A61B 5/7435* (2013.01); *A61B 5/021* (2013.01); *A61B 5/02438* (2013.01); *A61B 5/1112* (2013.01); *A61B 2562/0219* (2013.01)

(58) Field of Classification Search
CPC ................ A61B 5/7275; A61B 5/7435; A61B 2562/0219; A61B 5/1112; A61B 5/02438; A61B 5/021; A61B 5/7264; A61B 5/4809; A61B 5/02405; A61B 5/746; A61B 5/14551; A61B 2503/22; A61B 5/0402; A61B 5/6893; G08B 21/06; G61H 40/63; G16H 50/20
See application file for complete search history.

(56) References Cited

U.S. PATENT DOCUMENTS

2007/0032733 A1* 2/2007 Burton ................ A61B 5/4812
600/509
2015/0201853 A1* 7/2015 Hong ................ A61B 5/02427
600/301
2016/0071393 A1* 3/2016 Kaplan ................ B60K 28/066
340/539.12

OTHER PUBLICATIONS

Rios-Aguilar, Sergio, et al., "Variation of the Heartbeat and Activity as an Indicator of Drowsiness at the Wheel Using a Smartwatch," International Journal of Artificial Intelligence and Interactive Multimedia, vol. 3, No. 3, 2015.
Technology Against Drowsy Driving, "Technology Against Drowsy Driving," IoT, News, Software by Joanna Brzezinska, http://vorm.io/technology-drowsy-driving/, Oct. 2, 2017.
Kickstarter, "Protect Against Sleepy Driving and Monitor Pulse Any Where," https://www.kickstarter.com/projects/advicydrive/advicy-drive-safety-wearable-device-to-prevent-dro/, printed Oct. 2, 2019, published 2015.
Vicente, Jose, et al, "Drowsiness Detection Using Heart Rate Variability," Med. Biol. Eng. Comput, 54:297-937, 2016.
Coxworth, Ben, "Anti Sleep Pilot Detects Drowsy Drivers," New Atlas, https://newatlas.com/anti-sleep-pilot-monitors-driver-fatigue/17439/, Jan. 3, 2011.
StopSleep Presentation, Anti-Sleep Alarm, "Drive Safely Stay Alert with StopSleep," https://web.archive.org/web/20161029081937/http://www.stopsleep.co.uk:80/, Oct. 2017.

* cited by examiner

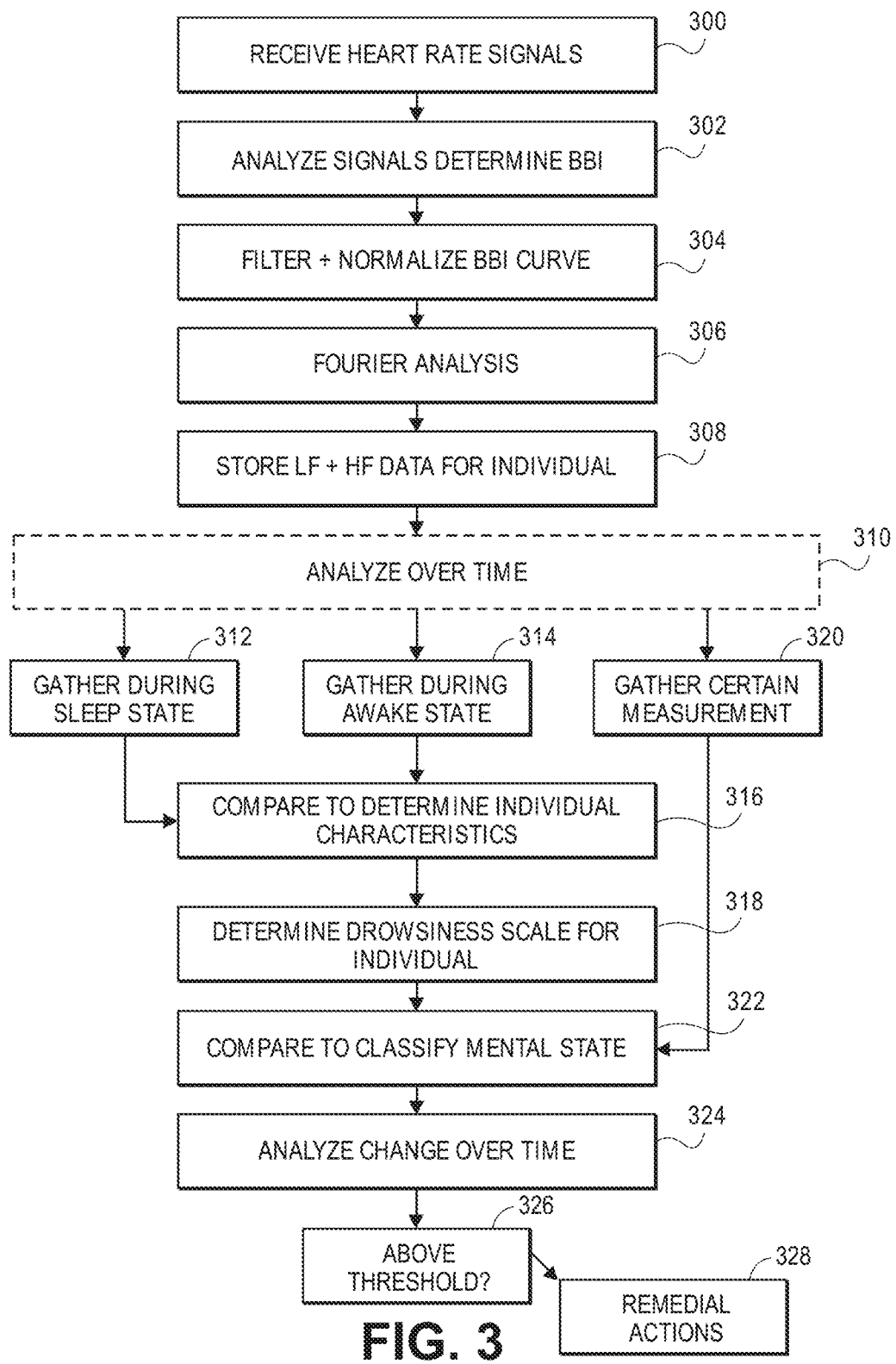

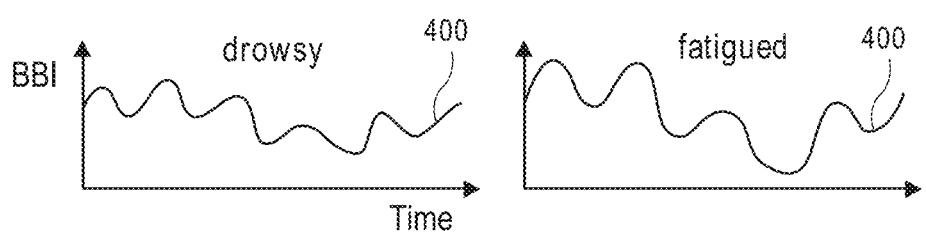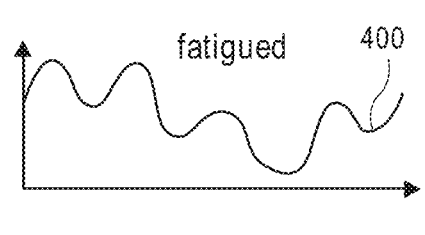
FIG. 4A  FIG. 4B
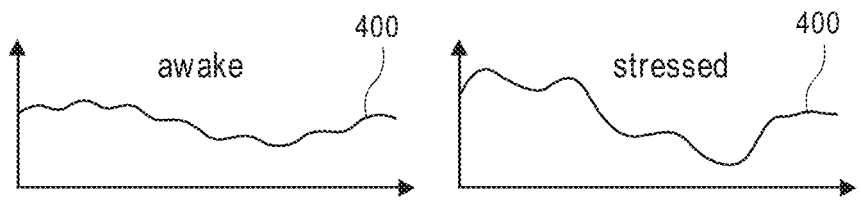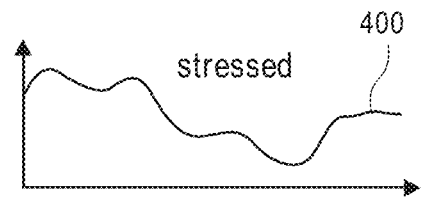
FIG. 4C  FIG. 4D

US 10,966,647 B2

DROWSINESS DETECTION

RELATED APPLICATIONS

This non-provisional patent application claims priority benefit, with regard to all common subject matter, of earlier-filed U.S. Provisional Patent Application No. 62/620,804, filed on Jan. 23, 2018, and entitled "DROWSINESS DETECTION" (the '804 Application).

This non-provisional patent application claims priority benefit, with regard to all common subject matter, of earlier-filed U.S. Provisional Patent Application No. 62/716,464, filed on Aug. 9, 2018, and entitled "DROWSINESS DETECTION" (the '464 Application). The '464 Application and the '804 Application are each hereby incorporated by reference in their entirety into the present application.

BACKGROUND

Various electronic devices may incorporate a heartrate monitor. For example, smartwatches, such as activity trackers and/or GPS watches, may incorporate or communicate with a heartrate monitor to measure a user's heartrate.

SUMMARY

In embodiments of the invention, a mobile electronic device utilizes a heartrate sensor (either internal or external) to provide an indication of a user's drowsiness level. Based upon the drowsiness level various alerts and other remedial actions may be provided. For example, the device may be configured to determine when a user is driving and provide vibration and auditory alerts if the user is drowsy.

In various embodiments, a mobile electronic device is operable to detect and display a mental state of a user such as drowsiness. The mobile electronic device includes a heartrate sensor, a processor, and a display. The heartrate sensor is operable to provide a heartbeat signal indicative of a heartbeat of the user. The processor is operable to: acquire a beat-to-beat interval based upon the heartbeat signal and determine a drowsiness level of the user based at least in part upon the beat-to-beat interval. The display is operable to display an indication of the drowsiness level.

This Summary is provided solely to introduce subject matter that is fully described in the Detailed Description and Drawings. Accordingly, the Summary should not be considered to describe essential features nor be used to determine a scope of the claims.

BRIEF DESCRIPTION OF THE DRAWINGS

The detailed description is described with reference to the accompanying figures. The use of the same reference numbers in different instances in the description and the figures may indicate similar or identical items.

FIG. 3 is a flow diagram showing steps of an exemplary method;

FIGS. 4A-4D are graphs showing a beat-to-beat interval curve of a heartbeat of the user;

DETAILED DESCRIPTION

Overview

Various mobile electronic devices measure the heartrate of a wearer or user. In some embodiments of the invention, the mobile electronic device is, or is associated with, a smartwatch. In other configurations, the device may be implemented as a standalone electronic device such as a smartphone, a wearable electronic such as an activity tracker, or an integrated electronics system such as an automobile infotainment system and/or aircraft avionics system.

In the following discussion, an example mobile electronic device and environment are first described. Exemplary procedures are then described that may be employed with the example environment, as well as with other environments and devices without departing from the spirit and scope thereof. Exemplary practical applications for the invention are then described, in addition to those discussed in other sections.

Example Mobile Electronic Device and Environment

Figure 1:
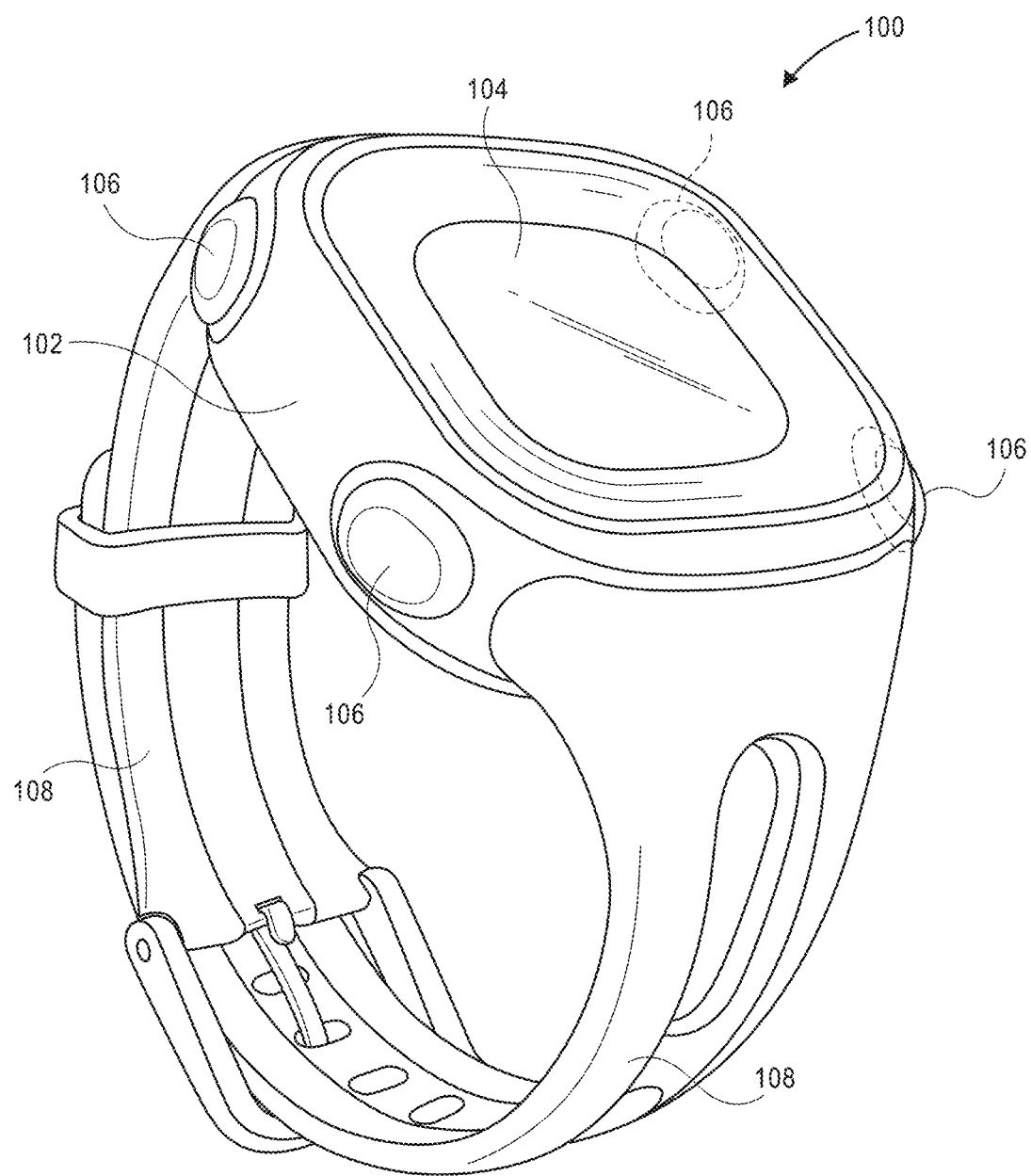
FIG. 1 is a perspective view of an exemplary mobile electronic device.
Figure 2:
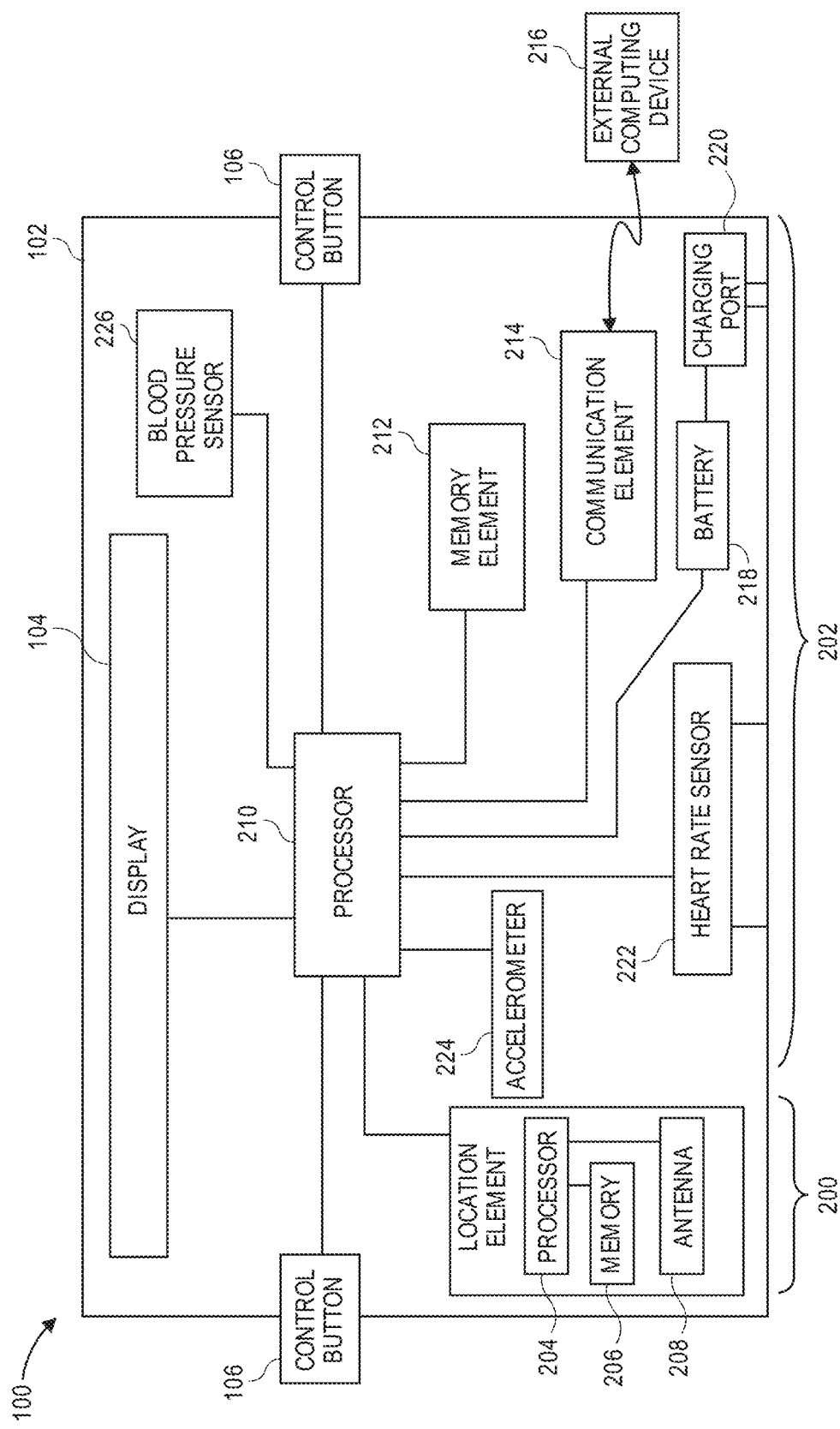
FIG. 2 is a schematic hardware diagram illustrating various components of the mobile electronic device.

FIG. 1 illustrates an example environment that is operable to perform the techniques discussed herein with an exemplary mobile electronic device 100. FIG. 2 illustrates various components of the mobile electronic device 100 shown schematically for clarity. The environment includes a mobile electronic device 100 operable to provide heartrate and perform an analysis thereof to determine a mental state of the user such as drowsiness. The mobile electronic device 100 may be configured in a variety of ways. For instance, the mobile electronic device 100 may be directly worn by the user or may provide sensor data to an external computing device that are executed in an external system for determining the mental state of the user. In the following description, a referenced component, such as mobile electronic device 100, may refer to one or more entities. Therefore, reference may be made herein to a single entity (e.g., the mobile electronic device 100) or multiple entities (e.g., the mobile electronic devices 100, the plurality of mobile electronic devices 100, etc.) using the same reference number.

FIG. 1 is a perspective view of a mobile electronic device 100 In embodiments of the invention. Mobile electronic device 100 is operable to provide fitness information and/or navigation functionality to the user of the device 100. The mobile electronic device 100 may be configured in a variety of ways. For instance, a mobile electronic device 100 may be configured for use during fitness and/or sporting activities and comprise a cycle computer, a fitness band, a sport watch, a golf computer, a smart phone providing fitness or sporting applications (apps), a hand-held GPS device used for hiking, and so forth. However, it is contemplated that the techniques described may be implemented in any mobile electronic device 100 that has or is associated with a heartrate sensor. Thus, the mobile electronic device 100 may also be configured as a portable navigation device (PND), a mobile phone, a hand-held portable computer, a tablet computer, a personal digital assistant, a multimedia device, a media player, a game device, automobile infotainment system, aircraft avionics system, combinations thereof, and so forth.

The mobile electronic device 100 includes a housing 102. The housing 102 is configured to house, e.g., substantially enclose, various components of the mobile electronic device 100. The housing 102 may be formed from a lightweight and impact-resistant material such as plastic, nylon, or combinations thereof, for example. The housing 102 may be formed from a non-conductive material, such a non-metal material, for example. The housing 102 may include one or more gaskets, e.g., a seal, to make it substantially waterproof or water resistant. The housing 102 may include a location for a battery and/or another power source for powering one or more components of the mobile electronic device 100. The housing 102 may be a singular piece or may include a plurality of sections. In embodiments, the housing 102 may be formed from a conductive material, such as metal, or a semi-conductive material. In some embodiments, the housing 102 is a watch housing 102 configured to be work by the user. In other embodiments, the housing 102 is another form factor.

The mobile electronic device 100 includes a display 104. The display 104 may, for example, include a liquid crystal display (LCD), a thin film transistor (TFT), a light-emitting diode (LED), a light-emitting polymer (LEP), and/or a polymer light-emitting diode (PLED). The display 104 may be capable of displaying text and/or graphical information. The display 104 may be backlit such that it may be viewed in the dark or other low-light environments. One example of the display 104 is a 100 pixel by 64 pixel film compensated super-twisted nematic display (FSTN) including a bright white light-emitting diode (LED) backlight. However, embodiments are not so limited. The display 104 may include a transparent lens that covers and/or protects components of the mobile electronic device 100. The display 104 may be backlit via a backlight such that it may be viewed in the dark or other low-light environments. The display 104 may be provided with a touch screen to receive input (e.g., data, commands, etc.) from a user. For example, a user may operate the mobile electronic device 100 by touching the touch screen and/or by performing gestures on the screen. In some embodiments, the touch screen may be a capacitive touch screen, a resistive touch screen, an infrared touch screen, combinations thereof, and the like. The mobile electronic device 100 may further include one or more input/output (I/O) devices (e.g., a keypad, buttons, a wireless input device, a thumbwheel input device, a trackstick input device, and so on). The I/O devices may include one or more audio I/O devices, such as a microphone, speakers, and so on.

In embodiments of the invention, the mobile electronic device 100 includes at least one control button 106. As illustrated in FIG. 1, the control button 106 is associated with, e.g., adjacent, the housing 102. While FIG. 1 illustrates four control buttons 106 associated with the housing 102, embodiments are not so limited. For example, the mobile electronic device 100 may include fewer than four control buttons 106, such as one, two, or three control buttons 106. Additionally, the mobile electronic device 100 may include more than four control buttons 106, such as five, six, or seven, for example. The control button 106 is configured to control a function of the mobile electronic device 100, such as the exemplary functions of the mobile electronic device 100 that are discussed below. Functions of the mobile electronic device 100 may include, but are not limited to, displaying a current geographic location of the mobile electronic device 100, mapping a location on the display 104, locating a desired location and displaying the desired location on the display 104, monitoring a user's heartrate, monitoring a user's speed, monitoring a distance traveled, calculating calories burned, and the like. In embodiments, user input may be provided from movement of the housing 102. For example, an accelerometer may be used to identify tap inputs on the housing 102 or upward and/or sideways movements of the housing 102. In embodiments, user input may be provided from touch inputs identified using various touch sensing technologies, such as resistive touch or capacitive touch interfaces. In any of these embodiments, the control button 106 may not be a physical button but instead a certain area of another structure.

The control button 106 of the mobile electronic device 100 may include buttons, dials, and other input structures (not illustrated). The input allows the user or other person to set up the mobile electronic device 100, provide commands to the mobile electronic device 100, check the status of the mobile electronic device 100, interact with the graphical user interface (described below), and perform other functions as may be necessary. In embodiments, the screen of the display 104 comprises a touch screen. For example, the touch screen may be a resistive touch screen, a surface acoustic wave touch screen, a capacitive touch screen, an infrared touch screen, optical imaging touch screens, dispersive signal touch screens, acoustic pulse recognition touch screens, combinations thereof, and the like.

In embodiments of the invention, the mobile electronic device 100 includes a strap 108. As illustrated in FIG. 1, the strap 108 is associated with, e.g., coupled to, the housing 102. The strap 108 may be a watch band or other strap for securing at least a portion of the mobile electronic device 100 to the user. For example, the strap 108 may be removably secured to the housing 102 via attachment of securing elements to corresponding connecting elements. Examples of securing elements and/or connecting elements include, but are not limited to hooks, latches, clamps, snaps, and the like. The strap 108 may be made of a lightweight and resilient thermoplastic elastomer and/or a fabric, for example, such that the strap 108 may encircle a portion of a user without discomfort while securing the housing 102 to the user. In other embodiments, the strap 108 may be formed of leather, metal, textile, or other material. The strap 108 may be configured to attach to various portions of a user, such as a user's leg, waist, wrist, forearm, and/or upper arm.

FIG. 2 illustrates a mobile electronic device 100, such as a watch, In embodiments of the invention. FIG. 2 illustrates schematically the various components that may be housed within the housing 102. In embodiments of the invention, the housing 102 can include a location determining component 200 and a performance monitoring component 202. The location determining component 200 is configured to provide a location indication that is indicative of a location of the user, or other location-deduced information such as speed. The performance monitoring component 202 is configured to provide at least one performance metric indicative of the user. Example performance metrics include heartrate, step count, blood pressure, and other metrics. In other embodiments, not illustrated, the housing 102 may include only the performance monitoring component 202. In still other embodiments, not illustrated, the housing 102 may include a processor configured to receive information from a location determining component 200 and/or a performance monitoring component 202, so as to perform the steps discussed below.

Various components of the mobile electronic device 100 may be disposed in or on one or more printed circuit boards. For example, the printed circuit board or boards may support a number of processors, microprocessors, controllers, microcontrollers, programmable intelligent computers (PIC), field-programmable gate arrays (FPGA), other processing components, other field logic devices, application specific integrated circuits (ASIC), and/or a memory that is configured to access and/or store information that is received or generated by the watch. The mobile electronic device 100 may implement one or more software programs to control text and/or graphical information on the display 104, as discussed herein.

The location determining component 200 may be a global positioning system ("GPS") receiver that is configured to provide geographic location information of the watch, or other mobile electronic device 100. The location determining component 200 may be, for example, a GPS receiver such as those provided in various products by GARMIN®. Generally, GPS is a satellite-based radio navigation system capable of determining continuous position, velocity, time, and direction information. Multiple users may simultaneously utilize GPS. GPS incorporates a plurality of GPS satellites that orbit the earth. Based on these orbits, GPS satellites can relay their location to a GPS receiver. For example, upon receiving a GPS signal, e.g., a radio signal, from a GPS satellite, the watch disclosed herein can determine a location of that satellite. The watch can continue scanning for GPS signals until it has acquired a number, e.g., at least three, of different GPS satellite signals. The watch may employ geometrical triangulation, e.g., where the watch utilizes the known GPS satellite positions to determine a position of the watch relative to the GPS satellites. Geographic location information and/or velocity information can be updated, e.g., in real time on a continuous basis, for the watch.

Location determining component 200 may also be configured to provide a variety of other position-determining functionality. Location determining functionality, for purposes of discussion herein, may relate to a variety of different navigation techniques and other techniques that may be supported by "knowing" one or more positions. For instance, location determining functionality may be employed to provide position/location information, timing information, speed information, and a variety of other navigation-related data. Accordingly, the location determining component 200 may be configured in a variety of ways to perform a wide variety of functions. For example, the location determining component 200 may be configured for outdoor navigation, vehicle navigation, aerial navigation (e.g., for airplanes, helicopters), marine navigation, personal use (e.g., as a part of fitness-related equipment), and so forth. Accordingly, the location determining component 200 may include a variety of devices to determine position using one or more of the techniques previously described.

In embodiments of the invention, the location determining component 200 may include a processor 204, a memory 206, and an antenna 208. The processor 204 may be one or more processors, controllers, and/or other computing devices. The memory 206 is operable for storing information accessed and/or generated by the processors or other computing devices. The processor may be electrically coupled with a printed circuit board and operable to process position determining signals received by the antenna 208. The location determining component 200, via the antenna 208, is configured to receive position determining signals, such as GPS signals from GPS satellites, to determine a current geographic location of the watch. The location determining component 200 may also be configured to calculate a route to a desired location, provide instructions, e.g., directions, to navigate to the desired location, display maps and other information on the display 104, and to execute other functions, such as, but not limited to, those functions described herein.

The location determining component 200, for instance, may use signal data received via a GPS receiver in combination with map data that is stored in the memory to generate navigation instructions (e.g., turn-by-turn instructions to an input destination or POI), show a current position on a map, and so on. Location determining component 200 may include one or more antennas 208 to receive signal data as well as to perform other communications, such as communication via one or more networks. The location determining component 200 may also provide other positioning functionality, such as to determine an average speed, calculate an arrival time, and so on.

The memory may store cartographic data and routing used by or generated by the location determining component 200. The memory may be integral with the location determining component 200, stand-alone memory, or a combination of both. The memory may include, for example, a removable nonvolatile memory card, such as a TransFlash card. The memory is an example of device-readable storage media that provides storage functionality to store various data associated with the operation of the mobile electronic device 100, such as the software program and code segments mentioned above, or other data to instruct the processor and other elements of the mobile electronic device 100 to perform the techniques described herein. A wide variety of types and combinations of memory may be employed. The memory may be integral with the processor, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth.

The antenna 208, for example, may be configured to receive and/or transmit a signal, such as a GPS signal. Antenna 208 may be any antenna capable of receiving wireless signals from a remote source, including directional antennas and omnidirectional antennas. Antenna 208 may include any type of antennas in which the length of the ground plane affects the efficiency of the antenna. In embodiments of the invention, the antenna 208 is an omnidirectional antenna having a ground plane. An omnidirectional antenna may receive and/or transmit in both orthogonal polarizations, depending upon direction. In other words, omnidirectional antennas do not have a predominant direction of reception and/or transmission. Examples of omnidirectional antennas include, but are not limited to, inverted-F antennas (IFAs) and planar inverted-F antennas (PIFAs). In contrast to omnidirectional antennas, directional antennas have a primary lobe of reception and/or transmission over an approximate 70 by 70 degree sector in a direction away from the ground plane. Examples of directional antennas include, but are not limited to, microstrip antennas and patch antennas.

In embodiments of the invention, the antenna 208 may be an embedded antenna. As used herein, an embedded antenna refers to an antenna that is positioned completely within a device housing 102. For example, antenna 208 may be positioned completely within housing 102. In some embodiments, antenna 208 may be an external antenna with all or a portion of the antenna 208 exposed from housing 102. As discussed, the location determining component 200 includes the antenna 208. The antenna 211 may be associated with, e.g., formed on and/or within, an antenna support assembly. Antenna 208 may be positioned on a top portion or one or more side portions of the antenna support assembly. As an example, the printed circuit board may support the bottom portion of the antenna support assembly. In some embodiments, the antenna support assembly and antenna 208 may be positioned in the center of the top surface, bottom surface, or to a side of the of the printed circuit board.

The performance monitoring component 202 tracks and analyzes various activities and sensor readings of the user. The performance monitoring component 202 may be positioned within the housing 102 and be coupled to the location determining component 200 and the display 104. The performance monitoring component 202 may receive information, including, but not limited to geographic location information, from the location determining component 200, to perform a function, such as monitoring performance and/or calculating performance values and/or information related to a watch user's movement, e.g., exercise. The monitoring of the performance and/or the calculating performance values may be based at least in part on the geographic location information. The performance values may include, for example, a user's heartrate, speed, a total distance traveled, total distance goals, speed goals, pace, cadence, and calories burned. These values and/or information may be presented on the display 104.

In embodiments of the invention, the performance monitoring component 202 may comprise a processor 210. The processor 210 may provide processing functionality for the mobile electronic device 100 and may include any number of processors, micro-controllers, or other processing systems, and resident or external memory for storing data and other information accessed or generated by the mobile electronic device 100. The processor 210 may execute one or more software programs that implement the techniques and modules described herein. The processor 210 is not limited by the materials from which it is formed, or the processing mechanisms employed therein and, as such, may be implemented via semiconductor(s) and/or transistors (e.g., electronic integrated circuits (ICs)), and so forth.

In FIG. 2, the mobile electronic device 100 is illustrated as including two processors 204,210. Each processor 204, 210 provides processing functionality for the mobile electronic device 100 and may include any number of processors, micro-controllers, or other processing systems, and resident or external memory for storing data and other information accessed or generated by the mobile electronic device 100. The processor 204,210 may execute one or more software programs that implement the techniques and modules described herein. It should also be appreciated that the discussed functions and methods performed by one of the processors 204,210 may be performed by any of the other processors 204,210.

It should be appreciated that FIG. 2 illustrates only one exemplary embodiment of the invention. In other embodiments, there is only a single processor in the mobile electronic device 100. The single processor receives the information from the set of various sensors discussed below FIG. 2 illustrates two separate processors 204,210 for demonstrative reasons. More or fewer processors could also be utilized in the mobile electronic device 100.

In embodiments of the invention, the performance monitoring component 202 may comprise a memory element 212. The memory element 212 is an example of device-readable storage media that provides storage functionality to store various data associated with the operation of the mobile electronic device 100, such as the software program and code segments mentioned below, or other data to instruct the processor 210 and other elements of the mobile electronic device 100 to perform the techniques described herein. A wide variety of types and combinations of memory may be employed. The memory element 212 may be integral with the processor 210, a stand-alone memory, or a combination of both. The memory element 212 may include, for example, removable and non-removable memory elements such as RAM, ROM, Flash (e.g., SD Card, mini-SD card, micro-SD Card), magnetic, optical, USB memory devices, and so forth. In embodiments of the mobile electronic device 100, the memory may include removable ICC (Integrated Circuit Card) memory such as provided by SIM (Subscriber Identity Module) cards, USIM (Universal Subscriber Identity Module) cards, UICC (Universal Integrated Circuit Cards), and so on. In other embodiments, there is only a single memory element in the mobile electronic device 100. FIG. 2 illustrates two separate memory elements 206,212, but more or fewer memory elements could also be utilized in the mobile electronic device 100.

In embodiments of the invention, the performance monitoring component 202 may comprise a communication element 214 for sending and/or receiving messages from an external computing device 216. An example of an external computing devices 216 may be a smartphone carried by the user, a personal computer utilized by the user, or other computing device. The mobile electronic device 100 may include a communication element 214 representative of communication functionality to permit mobile electronic device 100 to send/receive data between different devices (e.g., components/peripherals) and/or over the one or more networks. Communication element 214 may be representative of a variety of communication components and functionality including, but not limited to: one or more antennas; a browser; a transmitter and/or receiver; a wireless radio; data ports; software interfaces and drivers; networking interfaces; data processing components; and so forth. The mobile electronic device 100 may be configured to communicate via one or more networks with a cellular provider and an Internet provider to receive mobile phone service and various content, respectively. Content may represent a variety of different content, examples of which include, but are not limited to: map data, which may include route information; web pages; services; music; photographs; video; email service; instant messaging; device drivers; real-time and/or historical weather data; instruction updates; and so forth.

One or more networks may be utilized as a variety of different communication pathways and network connections, individually or in combinations, to communicate among various components. Thus, the one or more networks may be representative of communication pathways achieved using a single network or multiple networks. Further, the one or more networks are representative of a variety of different types of networks and connections that are contemplated including, but not limited to: the Internet; an intranet; a satellite network; a cellular network; a mobile data network; wired and/or wireless connections; and so forth. Examples of wireless networks include, but are not limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through universal serial bus (USB), Ethernet, serial connections, and so forth.

The communications element 214 includes one or more Network Interface Units. NIU may be any form of wired or wireless network transceiver known in the art, including but not limited to networks configured for communications according to the one or more standards. Wired communications are also contemplated such as through universal serial bus (USB), Ethernet, serial connections, and so forth. Mobile electronic device 100 may include multiple NIUs for connecting to different networks or a single NIU that can connect to each necessary network.

In embodiments of the invention, the performance monitoring component 202 may comprise a battery 218 with a charging port 220. The charging port 220 is an external power adapter receiving power from an external power source providing AC or DC power and, if necessary, transforming it appropriately for use by mobile electronic device 100.

The performance monitoring component 202 of various embodiments may include one or more sensors, such as a heartrate sensor 222, an accelerometer 224, and/or a blood pressure sensor 226. The heartrate sensor 222 may be an optical heartrate sensor configured to be worn by the user against the wrist or other body part. The heartrate sensor is discussed in more depth below. The accelerometer 224 is operable to measure steps and other movements of the user. The measured steps may be utilized in determining activity levels that may influence the other readings and determination described herein. The blood pressure sensor 226 and related functions thereof are discussed below.

Example Procedures

The following discussion describes procedures that can be implemented in a mobile electronic device 100. The procedures can be implemented as operational flows in hardware, firmware, software, or a combination thereof. These operational flows are shown below as a set of blocks that specify operations performed by one or more devices and are not necessarily limited to the orders shown for performing the operations by the respective blocks. The features of the operational flows described below are platform-independent, meaning that the operations can be implemented on a variety of device platforms having a variety of processors.

Embodiments of the invention may include a mental state measurement and display system. Determination of, or changes in the determined, blood pressure (BP), heartrate (HR) and/or heartrate variability (HRV) may be analyzed by the processor 210 of the mobile electronic device 100 to determine a stress level, drowsiness level, or other mental state for the user of mobile electronic device 100. The processor 210 may determine HRV based on fluctuations of time between successive heart beats identified in a cardiac (heartbeat) signal, which may be a component of a PPG signal generated based on a reflection of light output by one or more LEDs after the light has passed through skin that is proximate to the housing 102 of mobile electronic device 100.

In embodiments, autonomic nervous system activity may be analyzed and determined by the processor 210 to be stressful or relaxing events based on determined changes in HR and HRV of a cardiac signal. A memory element 212 of the mobile electronic device 100 may aggregate HR and/or HRV data over a period of time. The processor 210 may retrieve from memory element 212 the stored HR and/or HRV data and analyzed the data to determine an overall stress level of the user. The overall stress level, drowsiness level, or other determination may be presented to the user on display 104 of mobile electronic device 100, as discussed below.

The processor 210 also may determine and monitor blood pressure over a period of time to determine the change of stress level. Overall stress level may be presented on display 104 in a graphical manner, numeric manner, or any combination thereof. Based on output from an inertial measurement unit (e.g., accelerometer 224, gyroscope, etc.) within the mobile electronic device 100, the processor 210 may be able to determine one or more periods of activity or inactivity to associate with determined stress levels for the user of the mobile electronic device 100.

The processor 210 may retrieve from memory element 212 various prior BP, HR and/or HRV data measured over a first period of time and analyze the retrieved data to determine an overall stress level for the user of the mobile electronic device 100. The processor 210 may retrieve from memory BP, HR and/or HRV data measured over a second period of time and analyze the retrieved data to determine an instantaneous stress or relaxing responses for the user of the mobile electronic device 100. The second period of time may be shorter in duration than the first period of time. Additionally, the second period of time may occur before, during a portion of, or after the first period of time or the second period of time may occur the first period of time. These periods of time may also be referred to as a time T1 and a time T2.

The processor 210 may aggregate several instantaneous response values over a period of time to provide trending metrics. For example, trending metrics may provide insight to users about increasing, leveled (stable), or decreasing levels. The processor 210 may take historical data into consideration when determining trending metrics to better determine and predict the progression of a user's current and anticipated levels. Historical data may include information related to location, activity, time, or personal fitness, such as amount of exercise, recovery time, sleep metrics, and so on. In embodiments, the historical data may be detected by the processor 210 or input by the user.

In embodiments, the mental state (such as drowsiness or stress) level and the trending of that mental state may be categorized into different zones based on the magnitudes of each. For example, the processor 210 may express stress level zones as low, medium, and high. Other terms may be used to provide better granularity and understanding of determined stress levels and trends for a user. Similarly, the processor 210 may express trending zones as increasing, neutral, or decreasing.

FIG. 3 presents a flowchart illustrating the operation of a method of detecting a mental state of the user using embodiments of the invention. In particular, FIG. 3 illustrates the steps of receiving and analyzing heartrate signals, determining a mental state based upon the analysis, and utilizing the mental state in various ways.

In Step 300, the heartrate signal is received from the heartrate sensor 222. The heartrate signal is indicative of heartbeats as detected by the heartrate sensor 222. In Step 302, the heartrate signal is analyzed to determine heartrate variability and a beat-to-beat interval (BBI). Heartrate variability is the variation in time between consecutive heartbeats. The beat-to-beat interval may be graphed, such as shown in FIGS. 4A-4D. These four graphs show different combinations of results of the graphing. FIGS. 4A and 4B show larger short-term variations of the BBI curve 400 (larger high-frequency power), which is commonly assigned to drowsy states. FIGS. 4B and 4D show larger long-term variations of the BBI curve 400 (larger low-frequency power), which is commonly assigned to stressed states. The combination of stress and drowsiness (here called fatigue) means that you are drowsy lack the ready ability to relax. In this case both the SNS and the PSNS are very active.

In Step 304, the beat-to-beat interval is filtered and normalized to forms curve and identify beats. Filtering may include noise reduction, baseline compensation, and/or pulsation peak detection. Additionally or alternatively, filtering may include removing artefacts such as peaks not related to the pulsation. Filtering may also include QRS complex detection in the readings. Pulsation peaks are not as sharp as the events of heart contraction. The so-called "Windkessel vessels" (large elastic arteries near to the heart) buffer the acute blood streams caused by heart contractions. The buffered blood is released more continuously to the aorta. This protects the rest of the vessels in the body against overstain due to sharp blood pressure changes during a heart cycle. Smaller blood streams caused by incompletely filled ventricles in case of premature ventricular or atrial contractions (ectopic beats) are often completely buffered in the Windkessel vessels and not visible at all in the pulsation. Normalization may include completing incomplete data, such as based upon a poor PPG signal. Normalization fills in these gaps in the BBI sequence.

In Step 306, a Fourier analysis is performed on the identified curve. A Fourier transform of the BBI curve 400 may be known as a power spectral density (PSD). The discrete Fourier transform of the resampled BBI curve 400 shows the magnitudes of variations in that curve for different periods. In the example a variation with a period of 4 seconds (¼ Hz frequency) is shown. The power spectrum is a clear, sharp peak in case of a theoretical, perfectly sine-shaped curve with a given frequency. In practice, deviations from that perfect sine shape lead to blurred peaks in the power spectrum. Moreover, if the BBI curve 400 shows variations with different periods the power spectrum is a superposition of multiple peaks.

FIGS. 5A-5D show exemplary results of a Fourier analysis. The low-frequency (LF) and high-frequency (HF) powers are the sizes (heights and widths) of the LF and HF peaks in the power spectrum. The LF and HF powers correlate to the strengths of the long-term and short-term variations of the heartrate signal. Because the power spectrums will not perfectly match any of the models, a degree or score of the diagnosis may be calculated. This degree or score may be presented to the user in the graphical user interface and/or utilized in another practical application (such as an alert or integration into an external system). The system may determine an LF threshold and/or HF threshold to determine the diagnosis.

Figure 5A:
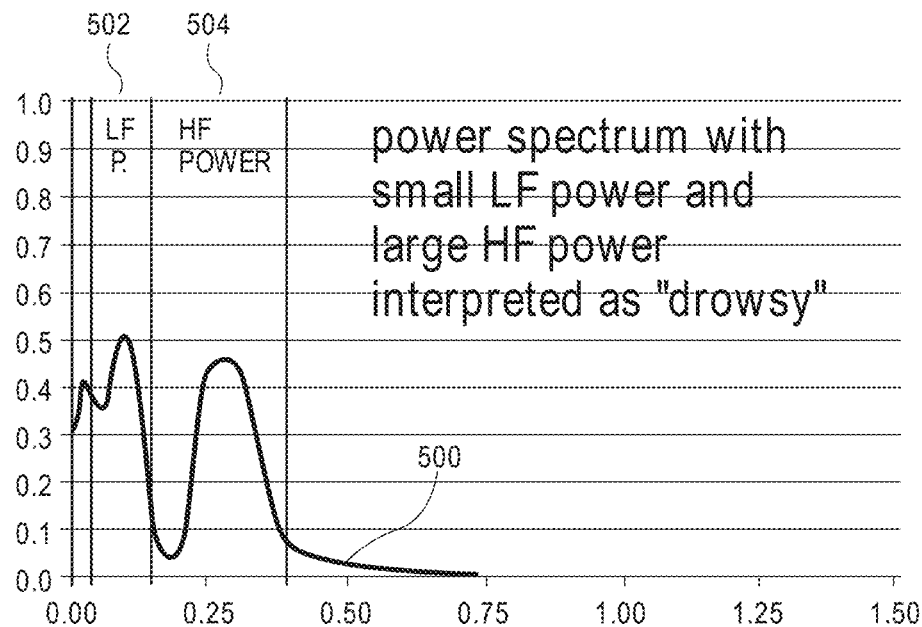
FIGS. 5A-5D are graphs showing a power spectrum based upon a Fourier transform of the beat-to-beat interval curve.
Figure 5B:
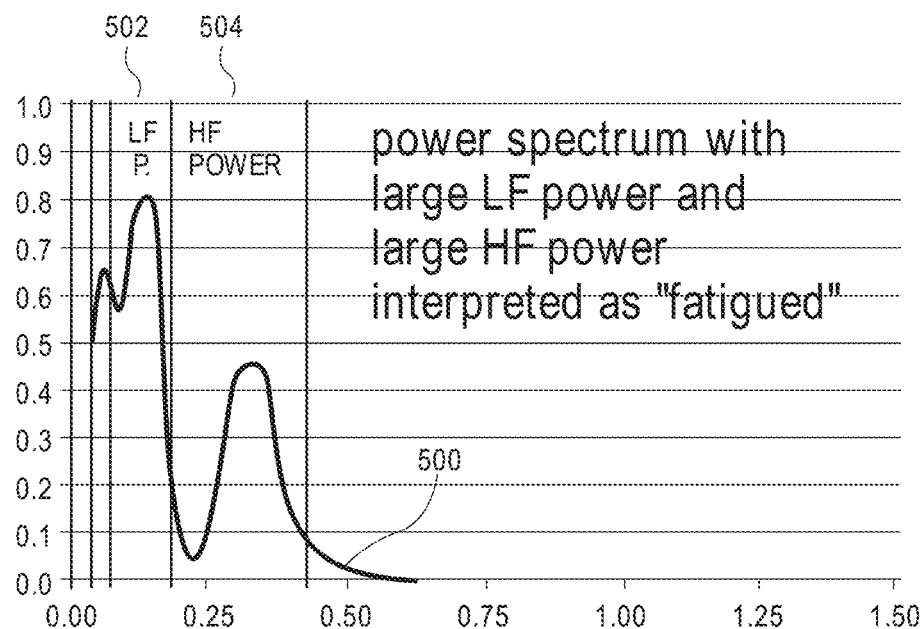
Figure 5C:
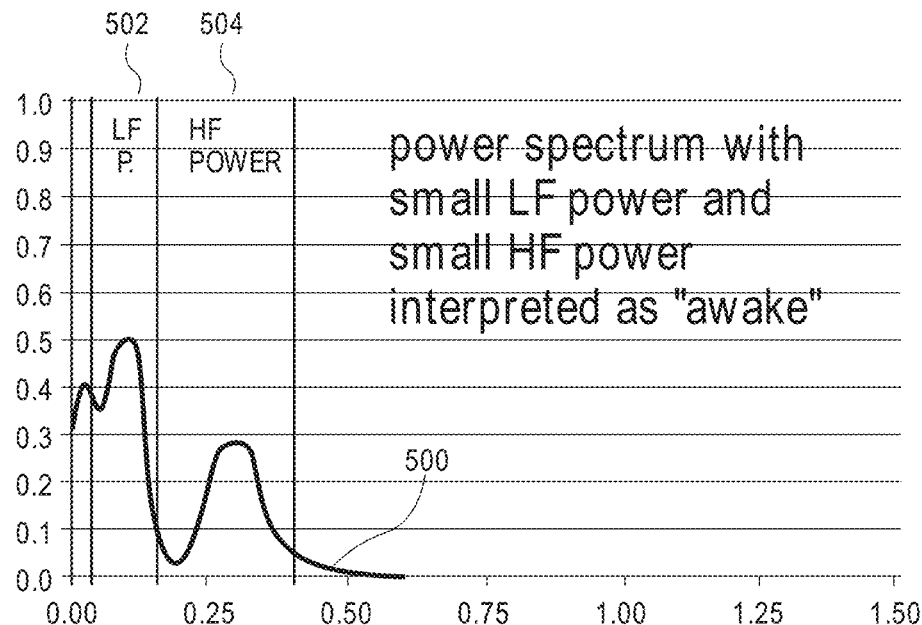
Figure 5D:
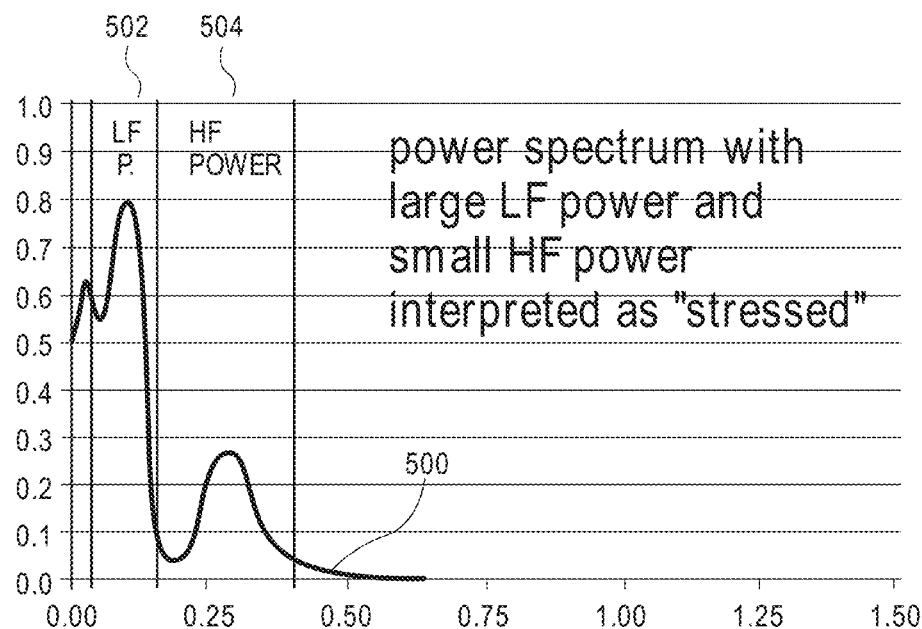

The LF and HF powers are shown in FIGS. 5A-5D, illustrating four exemplary distributions and the common diagnosis associated with each. FIG. 5A shows a power spectrum presenting a relatively small LF power and a relatively large HF power, which the system will typically interpret as "drowsy." Thus, the processor 210 may determine upon the low-frequency power being under an LF threshold and upon the high-frequency power being above an HF threshold that this is indicative that the mental state of the user is drowsy. FIG. 5B shows a power spectrum presenting a relatively large LF power and a relatively large HF power, which the system will typically interpret as "fatigued." Thus, the processor 210 may determine upon the low-frequency power being above an LF threshold and upon the high-frequency power being above an HF threshold that this is indicative that the mental state of the user is fatigued. FIG. 5C shows a power spectrum presenting a relatively small LF power and a relatively small HF power, which the system will typically interpret as "awake." Thus, the processor 210 may determine upon the low-frequency power being under an LF threshold and upon the high-frequency power being under an HF threshold that this is indicative that the mental state of the user is awake. FIG. 5D shows a power spectrum presenting a relatively large LF power and a relatively small HF power, which the system will typically interpret as "stressed." Thus, the processor 210 may determine upon the low-frequency power being above an LF threshold and upon the high-frequency power being under an HF threshold that this is indicative that the mental state of the user is stressed. As such, these diagnoses may be linked and scaled against one another.

As illustrated in FIGS. 5A-5D, very-low-frequency power (VLF) may be disposed below the LF area of the graph (though not labeled). VLF is indicative of a gradual drift in the heartrate over minutes. There may also be very-high-frequency power (VHF) above the HF are of the graph. VHF is caused by noise in the data, and thus are not resulting from a physiological cause but from the measurement of the pulsation.

In the examples shown, the VLF is shown as less than 0.04 Hz and the VHF is shown as more than 0.40 Hz. It should be appreciated that these values may change by the individual, as determined based upon a baseline for the user established over time. The tail of the power spectrum shows irregularities in the resampled BBI curve 400 caused by remaining, non-eliminated noise in the PPG signal. The very small section in front of the LF section, less than 0.04 Hz (the very low frequency/VLF section), represents a slow drift of the heartrate over several minutes, for example due to changed physical activity. Note that the y-axes of power spectra graphs display a normalized scale (the highest peak of the spectra normalized to 1.0). The actual heights of the spectra can be read from the "normalization factor" given in the graphs.

There are several approaches for computing the LF power and the HF power (and the sharpness of both peaks): Either by simple summation over the discrete values of the spectra in the corresponding sections. Or by fitting a curved model to the spectra and then computing the volumes below the LF and HF peaks of the fitted model. The tails (e.g., VLF and VHF) of the spectra are ignored for the optimization of the model.

It should be appreciated that determining the diagnosis based upon analysis of the features from the HRV is accompanied with noise and other inaccuracies. Furthermore, apart from the technical and processing issues, the physiology of the nervous system and the heart regulation is not perfectly stable. Therefore, for example, awake states can be closer to sleeping states than states representing a little drowsiness. And those can be closer to sleeping states than very drowsy states.

In Step 308, information from the Fourier analysis, such as the low-frequency power and the high-frequency power, is stored. The information from the Fourier analysis may be stored along with other known information about the user at that time. This other known information about the user will be utilized by the processor 210 in further refining the diagnoses. For example, the information from the Fourier analysis may be stored with information related to activity level, sleep or awake state, user input (e.g., a response to a query presented to the user asking the user to rate their drowsiness level), time of day, time relative to another event (e.g., time awake that day), and other information.

Figure 6:
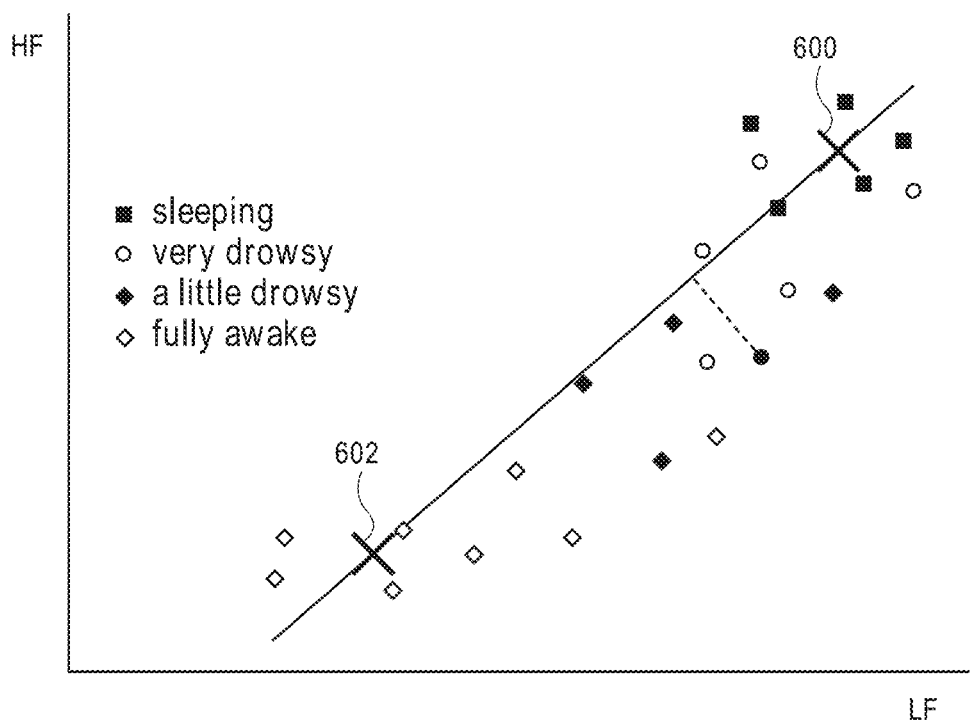
FIG. 6 is a personalized drowsiness scale for the user.

In Step 310, the steps of the method are performed over time to acquire multiple samples. In Step 312, samples are gathered during sleep periods. Samples may be determined to be during sleep periods based upon the time of day, activity level, and other indicia. In Step 314, samples are gathered during active periods. These samples may also be determined to be during active periods based upon the time of day, activity level, selection of the control button 106, the activation of an activity tracker function of the mobile electronic device 100, or other indicia. In Step 316, the samples are compared to determine individual characteristics. For example, the samples may be graphed as shown in FIG. 6 or compared mathematically. Because every user has different physiological properties, the processor 210 gathers samples over time to determine the proper diagnosis for the user. The processor 210 may provide results to the user while continuing to refine and improve the readings. In some embodiments, the drowsy (non-sleeping) data is distinct from the sleeping data for that person. This may be based upon how a user feels and rates their drowsiness.

Based upon this analysis, in Step 318, a personalized drowsiness scale is created. The drowsiness scale may determine the above-discussed LF threshold and HF threshold based at least in part upon the average awake value and the average sleep value. FIG. 6 shows an exemplary analysis over time. Various samples are plotted on a graph comparing LF to HF, along with a diagnosis associated (which may be calculated before, during, or after this analysis). Based upon the analysis over time, the processor 210 determines a standard sleeping value 600 and a standard awake value 602. Other samples are compared to these standard values 600, 602 to determine a diagnosis. Even in theory the data is not necessarily aligned on a straight line between the standard values 600,602. Apart from variations due to noisy data, the form of the cloud of data depends on the exact physiology of the nervous system and the heart regulation. The learned awake-to-drowsy axis (shown as a line in FIG. 6) defines the scale 0 to 100 for the drowsiness. Values below 0 and above 100 are possible for very extreme states (more extreme than the learned standard sleep value 600 and standard awake value 602).

In Step 320, a certain test sample is gathered after the personalized drowsiness scale is created. New samples are compared to their position along that awake-to-drowsy axis. Thus, a numerical value may be assigned to the new sample based upon the position along the awake-to-drowsy axis of the personalized drowsiness scale. These numerical values may be utilized in the below discussed practical applications and/or shown in the below discussed user interface.

In Step 322, the certain test sample is compared to the personalized drowsiness scale to classify the mental state of the person. For example, the classified mental state may be categorized (e.g., highly drowsy). In Step 324, the test samples are compared over time to determine trends and changes over time. These trends and changes may also be used to determine alerts and other functions based upon the values. For example, if the user is driving and highly drowsy, but their drowsiness level is decreasing, the system may refrain from taking any actions and continue to monitor the user. Alternatively, if the user is driving and at a moderate drowsiness level, but their drowsiness level is rapidly increasing, the system may alert the driver or take other remedial actions (even though the drowsiness level is lower in the second example).

In Step 326, the processor 210 determines if the drowsiness level is over a certain threshold. The threshold may be based upon the user's activity (e.g., driving may have a lower threshold than sedentary activity). If the user's drowsiness level is not over the threshold, the processor 210 continues to take samples and analyze over time.

If the user is over the threshold, in Step 328 the user may be presented information determined to help reduce the user's current level (a "remedial action"). The remedial action may include, but is not limited to, haptic and/or audible notifications; verbiage, icon(s), color(s), and/or animation(s) presented on display 104 of the mobile electronic device 100. Information that may be presented to reduce a current stress level may include stress-coping mechanisms (e.g., breathing exercises) and/or relaxation activities (e.g., mild physical exercise). Remedial action information and/or reminders thereof may time out after a certain period of time and may be removed with greater intensity or shorter interval for calls to action and/or reminders going forward.

In embodiments of the invention, the processor 210 may determine body energy level. Stress and relaxing responses may be accumulated and combined with the evaluation of physical loadings resulting from exercise sessions and/or daily activities experienced throughout the day with HR and HRV monitoring. Sleep and other relaxing activities, such as naps, recreation, and so on, may also be included for holistic body energy level considerations. The processor 210 may evaluate recovery and depletion stage for the body energy level based on changes in a determined HRV with the amount and intensity of physical activities taken into account. Time spent accumulating and consuming body energy may be measured and tracked by the processor 210 to determine and indicate a duration of energy recovery and depletion, and the mobile electronic device 100 may provide feedback to the user regarding the same. Recovery time after exercise may be dynamically adjusted based on continuous considerations of body energy level facilitated by HR and HRV measurements.

In embodiments of the invention, the processor 210 may determine recharging, and discharging states based on the trend of the body energy level. The rates of recharging and discharging may be calculated based on the combination of incremental changes in body energy level and changes in instantaneous stress and/or relaxing response. The discharge rate of body energy level may include, but is not limited to, intensity and number of stressful events, loading of physical activities, and/or intensity of physical loadings. The recharge rate of body energy level may be calculated based on HRV and/or HR and combined with some other contextual information, such as location, time of day, activities previously engaged in, and so on.

In embodiments of the invention, the mobile electronic device 100 may determine a relaxation level for a user and present, on a display 104 of the mobile electronic device 100. After experiencing periods of stress weighted by intensity the user's determined relaxation level is diminishing (and corresponding stress level is rising). The processor 210 may stop illuminating one or more segments based on determined periods of stress (e.g., after 5 minutes of high stress, 15 minutes of medium stress, 30 minutes of low stress, etc.). If recovery is determined to occur, the processor 210 may illuminate segments that were previously illuminated, in full or in part, either at once or slowly over time based on determined stress levels. If a recovery is not determined to have occurred after a predetermined, threshold length of time, additional segments may stop being illuminated (e.g., previously illuminated short bars may disappear in turn after 3 minutes of high stress, 8 minutes of medium stress, 15 minutes of low stress, etc.). If recovery is determined to occur, the previously illuminated bars may illuminate once again, in full or in part, either at once or slowly over time. Recovery times, stress periods, and any threshold values may be pre-determined values stored in memory element 212, calculated dynamically by the processor 210, or input (supplied) by the user.

These samples and analyses may also be used to compare users and determine a default settings or values (such as for the personalized drowsiness scale discussed above). The samples of multiple different users may be shown as a cloud of data (not illustrated). After learning the awake and drowsy states from the data for a first person, awake and drowsy states for a second person may be more easily determined. The second person may develop a second personalized drowsiness scale that shifts or changes from the first personalized drowsiness scale.

Figure 7:
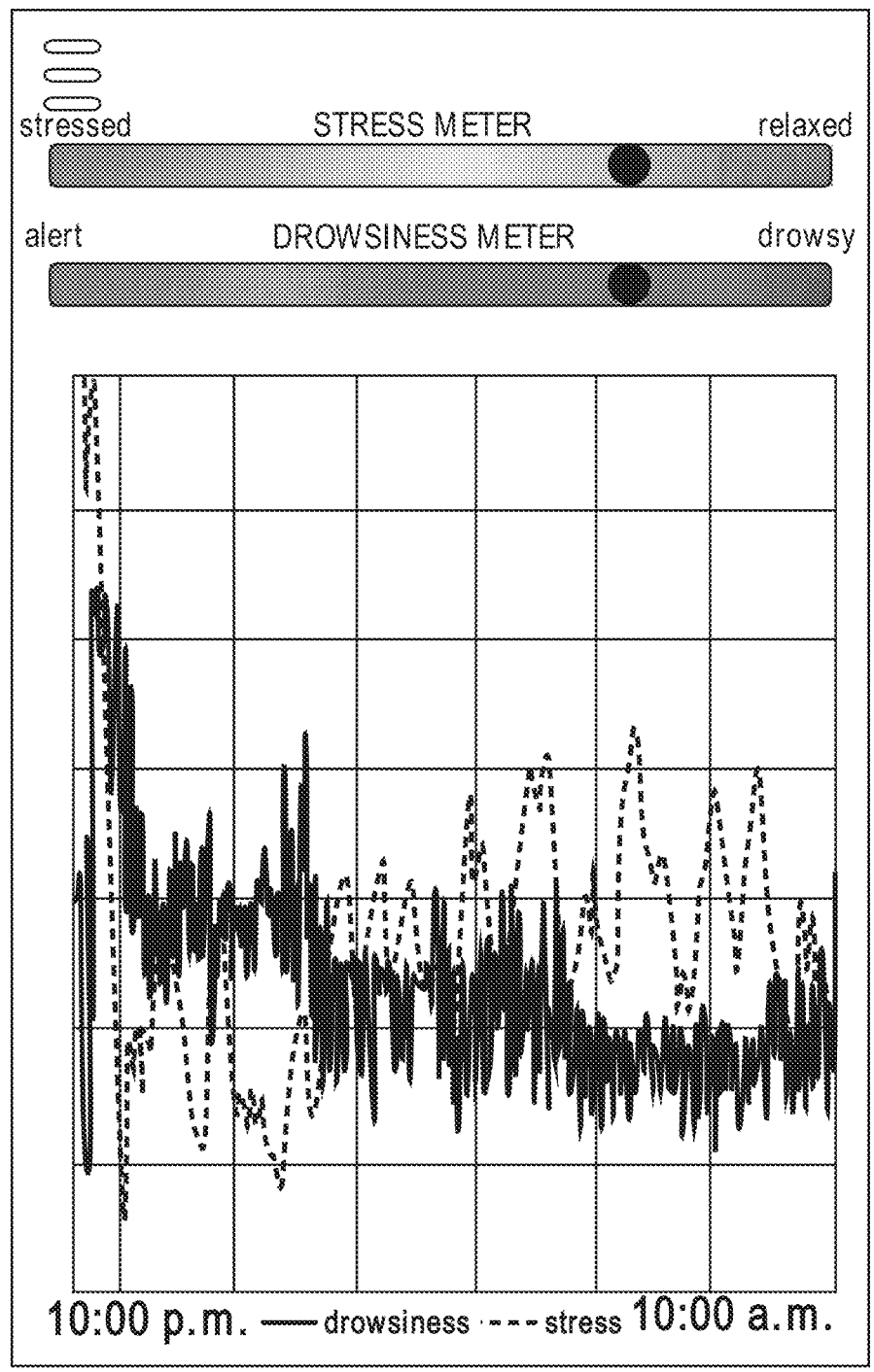
FIG. 7 is a graph of drowsiness and stress for the user over time.

These samples and analyses may also be utilized to measure stress and other mental states. As such, the stress level and drowsiness level may be compared against each other to provide the user with a more complete view of their physiological status. As an example, a graph comparing stress level and drowsiness level is shown in FIG. 7. This exemplary graph shows how the stress level and drowsiness level change over time throughout a day (or other time period).

Generally, any of the functions described herein may be implemented using software, firmware, hardware (e.g., fixed logic circuitry), manual processing, or a combination of these implementations. The terms "module" and "functionality" as used herein generally represent software, firmware, hardware, or a combination thereof. In the case of a software implementation, for instance, the module represents executable instructions that perform specified tasks when executed on a processor, such as the processor 210 of the mobile electronic device 100. The program code may be stored in one or more device-readable storage media, an example of which is the memory element 212 of the mobile electronic device 100.

Example Practical Applications

Embodiments of the invention may be directed to or involve various practical applications. Examples of practical applications may be discussed but should not be considered limiting. Embodiments of the invention may be directed to a practical application without any of the below, or other practical applications may also be implemented. Some embodiments of the invention may be integrated into or associated with a practical application or provide information to one of the practical applications.

A first exemplary practical application is in displaying results, values, trends, diagnoses, and other information on a graphical user interface (as discussed below). The graphical user interface displays information to the user, such that the user may utilize the information in various practical ways. Upon determining the user's own mental state, the user may make various decisions about physical activities. For example, the user may decide to sleep, drink coffee, or do a more intense workout.

A second exemplary practical application is in or with a driver activation system. A driver activation system may provide visual, acoustical, haptic, tactile, or other sensory feedback to the user that is driving. For example, the driver activation system may alert the user of their current drowsiness level. The driver activation system may recommend that the driver take a break or perform other actions to reduce the drowsiness. The other actions may include specific exercises for the driver to perform while driving or during the break. These specific exercises are designed to overcome the drowsiness or reduce its effects on impairing the driving by the user. Examples of exercises may include breathing exercises, certain body movements, or sport exercises to be performed outside of the vehicle to increase the heartrate and provide other drowsiness-reducing benefits. The other actions recommended may include changing the temperature settings, music, lighting, or other settings in the vehicle. In some embodiments, the recommended actions may be taken by the vehicle automatically without any user input.

A third exemplary practical application is in or with an advanced driver-assistance system (ADAS). An advanced driver-assistance system helps the driver in some way while the driver is operating the vehicle. Embodiments of the invention may provide an input to an ADAS to allow or instruct the ADAS to perform various functions. For example, the ADAS may implement an adaptive restrictiveness on various functions like lane departure assistants, speed warnings, curve warnings, distance warnings, or other functions based upon a drowsiness level. As a specific example, if the driver is drowsy, the ADAS may alert the driver (or steer the vehicle) more quickly over a more minor lane departure than if the driver is alert. The ADAS may also adaptively learn of driver habits in a drowsy state so as to more quickly and effectively assist the driver. The ADAS may additionally or alternatively track the driver habits at various levels of drowsiness to detect certain driving habits associated with those drowsiness levels. In other embodiments, the ADAS may assist, guide, or instruct the driver in bringing the vehicle to a stopped position if a high-level of drowsiness is detected.

A fourth exemplary practical application is in or with a semi-automatic driving system. A semi-automatic driving system at least partially controls the vehicle and can override the driver actions under certain conditions. For example, the semi-automatic driving system may take over control of the vehicle and bring the vehicle to a stop upon detecting a high-level of drowsiness in the driver. As another example, the semi-automatic driving system may take over control of the vehicle upon the driver taking the vehicle out of the lane (or failing to take an action to keep the vehicle in the lane) at a lower threshold if a high-level of drowsiness is detected.

A fifth exemplary practical application is in or with a navigation device, such as a portable navigation device. The navigation device may be a component of the vehicle, a stand-alone component located in the vehicle, a smart phone of the user, a smartwatch worn by the user, or other device that assists the user in navigating. The navigation device may select a certain route, or change to a certain route, in response to the drowsiness level of the user. The navigation device may determine, or be programmed to implement, various routes or route types that affect drowsiness. The navigation device may learn how various routes, route types, or combinations thereof affect certain drivers. Based upon this information, the navigation device may select or recommend routes to the user. For example, if the driver is at a moderate level of drowsiness, the navigation device may select a route designed to reduce or at least not increase the drowsiness level of the user. Thus, the navigation device may route the user off of a highway that would otherwise be routed so as to not increase the drowsiness of the driver. The navigation device may also balance faster arrival with low drowsiness risk.

A sixth exemplary practical application is in or with personalized driving recommendations, which may be implemented on various different devices. Personalized driving recommendations may help a driver plan a certain trip before the trip begins. Based upon the driver-specific and/or generally known drowsiness information, certain trip characteristics may be advantageous or disadvantageous for a certain driver. Examples of personalized driving recommendations may include certain travel days, certain travel weather conditions, certain travel times of day, previous activities, previous sleep durations, travel durations, and other considerations. For example, if the driver indicates that a certain trip is upcoming, the personalized driving recommendations may recommend leaving after a certain time of morning, getting a certain amount of sleep the night before, taking certain planned breaks along the route, avoiding certain road types after a certain time of day, or other recommendations. These recommendations may be presented to the driver, implemented into a route, or utilized in other ways.

A seventh exemplary practical application is in or with a combination with other drowsiness-detection systems. Certain systems exist to detect or approximate drowsiness. For example, some systems may attempt to detect drowsiness based upon visual analysis of the driver, analysis of the driving actions of the driver, or the like. Embodiments of the invention which detect drowsiness and other mental states from the heartrate variability as measured at the wrist of other body part of the driver may be utilized to supplement or complement these other systems. Thus, these systems may have multiple different types of sensors to detect drowsiness so as to make more robust decisions and to compensate for other faulty or less-accurate sensors.

An eighth exemplary practical application is in or with a commercial fleet management system. Fleet management systems remotely monitor vehicles and drivers. Embodiments of the invention may be implemented into a fleet management system to further monitor a drowsiness level of the driver. Based at least in part on the drowsiness information, the fleet management system may adapt the schedule of the driver, send messages to the driver and/or a dispatcher. The fleet management system may also perform long term optimization of schedules and/or routes based upon drowsiness information across the fleet. The drowsiness information may also be tracked for a particular driver to demonstrate good driving behavior and/or drowsiness level at a certain time (such as a vehicular collision).

It should be appreciated that while the above-discussed exemplary practical applications were directed to automobiles, some practical applications of the invention may be directed to aviation applications, marine applications, locomotive applications, and other vehicle types. It should also be appreciated that while the above-discussed exemplary practical applications were directed to the detection of drowsiness, some practical application of the invention may be directed to other detected mental states.

In embodiments of the invention, readings and determinations made herein may be utilized in various ways. As a first example, insurance companies may provide a discount to customers that monitor their drowsiness level before or while operating their vehicle. The discount may attach to never driving above a certain drowsiness level, implementing a drowsiness mitigation system such as those discussed above, or other quantifiable steps that a driver may take. As a second example, healthcare providers may monitor the health of patients and other people over time. Drowsiness and other mental state information may allow the healthcare provider to draw conclusions about the impact that life style choices, work conditions, sleep patterns, and other criteria have on health. The healthcare provider may also make user-specific recommendations, such as lifestyle changes or recommendations to visit the healthcare provider.

Example User Interface

In embodiments, the mobile electronic device 100 includes a user interface, which is storable in memory element 212 and executable by the processor 210. The user interface is representative of functionality to control the display 104 of information and data to the user of the mobile electronic device 100 via the display 104. In some implementations, the display 104 may not be integrated into the mobile electronic device 100 and may instead be connected externally using universal serial bus (USB), Ethernet, serial connections, and so forth. The user interface may provide functionality to allow the user to interact with one or more applications of the mobile electronic device 100 by providing inputs via the touch screen and/or the I/O devices. For example, the user interface may cause an application programming interface (API) to be generated to expose functionality to an application to configure the application for display by the display 104 or in combination with another display. In embodiments, the API may further expose functionality to configure the application to allow the user to interact with an application by providing inputs via the touch screen and/or the I/O devices. Applications may comprise software, which is storable in memory element 212 and executable by the processor 210, to perform a specific operation or group of operations to furnish functionality to the mobile electronic device 100. Example applications may include fitness application, exercise applications, health applications, diet applications, cellular telephone applications, instant messaging applications, email applications, photograph sharing applications, calendar applications, address book applications, and so forth.

In some embodiments of the invention, the user interface may include or be displayed in a browser, such as on the external computing device. The browser enables the mobile electronic device 100 or external computing device to display and interact with content such as a webpage within the World Wide Web, a webpage provided by a web server in a private network, and so forth. The browser may be configured in a variety of ways. For example, the browser may be configured as an application accessed by the user interface. The browser may be a web browser suitable for use by a full resource device with substantial memory and processor resources (e.g., a smart phone, a personal digital assistant (PDA), etc.). However, in one or more implementations, the browser may be a mobile browser suitable for use by a low-resource device with limited memory and/or processing resources (e.g., a mobile telephone, a portable music device, a transportable entertainment device, etc.). Such mobile browsers typically conserve memory and processor resources but may offer fewer browser functions than web browsers.

In other embodiments, the user interface may include or be displayed directly on the display 104. The user interface may include a graphical depiction of a sensor reading, a diagnosis, a trend indication, and other information. The user interface may also show alerts and other notifications. The user interface may provide an overall view of the current situation of the user, as determined by the processor 210. In some embodiments, the user interface may be disposed in a pop-up window on the primary display 104 of the mobile electronic device 100, in a permanent window on the primary display, in a heads-up display ("HUD") on a vehicle, in a multi-function display ("MFD"), in a dedicated display, or in another display.

FIGS. 8A-8E show exemplary user interfaces that may be presented on display 104 to communicate determined drowsiness levels, stress levels, and ongoing trends on a mobile electronic device 100 (or other device) in accordance with embodiments of the invention. The user interface 800 may present a score icon 802, a scale icon 804, a scale indicator icon 806, a diagnosis icon 808, a trending icon 810, or some combination thereof. It should be appreciated that FIGS. 8A-8E show an exemplary user interface for a watch face (such as the watch shown in FIG. 1); however, the user interface may be configured to appear on a smartphone, a vehicle display, or other display.

The score icon 802 can be expressed in any of several forms. A first exemplary form is a numerical value. The numerical value could be expressed from 0 to 100, such that 0 is a theoretical minimum score and 100 is a theoretical maximum score (intermediate values being in the range of 1 to 99). In other embodiments, the score may have a numerical value from −100 to +100. For example, the score may be expressed as an awake-drowsiness scale such that −100 is completely drowsy and +100 is completely awake. In yet other embodiments, the numerical value is a summation of factors with no theoretical maximum or theoretical minimum. A second exemplary form is a letter grade, such as an "F" for dangerously drowsy and an "A" for completely awake (intermediate values being "B," "C," and "D"— possibly including plusses and minuses). A third exemplary form may be a color system in which red is drowsy and green is fully awake (intermediate values being on the color spectrum between red and green). A fourth exemplary form may be a simple binary designation. The binary designation definitely states whether the system believes the user to be drowsy or not. In this and other forms, the system may presume that the user is fully awake until the determination of the mental state.

The scale icon 804 may include one or more bars of a gauge shape, thermometer shape, or other scale shape indicative of how the score icon 802 compares with the range of possible values. This is because the score icon alone may not convey to the user the severity level or otherwise put the score icon into context. The scale icon therefore may have colored sections indicative of a severity level, as shown in FIGS. 8A-8D. The scale indicator icon 806 is displayed at least partially on or otherwise associated with the scale icon to demonstrate where the score icon falls within the range. The scale indicator icon may be an arrow, line, or other shape. In some embodiments, the scale indicator icon is shown by filling the scale icon to a certain extent. For example, the colors of the scale icon may only be shown to the extent that they are less than (or more than) the location of the scale indicator icon.

The diagnostic icon 808 presents information to the user related to the other icons. For example, the diagnostic icon may include information related to a categorization of the score icon, the type of score icon that is being displayed, a general value for the score icon, trend information, and other information related to the determined mental state. The diagnostic icon may help the user interpret the other icons displayed on the user interface. The trend may be shown to the user in any of numerous ways The trending icon 810 presents information related to a trend in the determined mental state, if such information is available. For example, the trending icon 810 one or more colors to communicate the rate or pace at which the determined stress level or drowsiness level is changing and the direction (increasing or decreasing) of the change. The trending icon may be in the form one or more bars, arrows, graphs, or other symbols. The trending icon may be static or animated. Animated trending icons may utilize a speed of the animation or other animation characteristics to demonstrate the trend. For example, the illustrated bar may be moving upward to indicate an increasing trend, with the speed of the movement indicative of the rate of increase. The trending icon may also present certain colors or other indications of whether the trend is positive or negative.

For example, as shown in user interface 300, a plurality of bars (3) are presented under the spectrum to indicate that the user's stress level is changing at a slower pace as the trend of stressing. The presented bar(s) are illuminated red to indicate that the change in determined stress level is increasing. Alternatively, the presented bar(s) may be illuminated green to indicate that the change in determined stress level is decreasing.

Figure 8A:
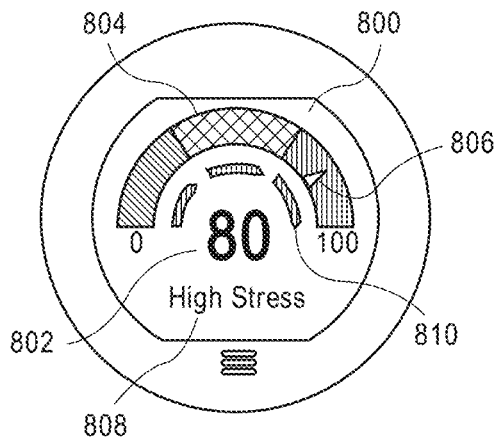
FIGS. 8A-8E show various embodiments of a graphical user interface depicting icons related to a detected mental state.

FIG. 8A shows a first exemplary user interface. In this exemplary user interface, the scale indicator icon, shown as an arrow, points to a certain portion of the scale icon (which may be colored red, for example). The location of the scale indicator icon is indicative that the user's determined level is high. Additionally, the score icon is shown as a large numeric '80' so as to indicate that the user's determined stress level is 80 within a range of 0 to 100. A diagnostic icon is shown as the text "High Stress" is presented under the score icon. The diagnostic icon shows the user that the other values presented on the user interface are related to stress (as opposed to another mental state such as drowsiness). Finally, the trending icon is shown as a series of three bar arrows pointed toward an increasing of the scale. The trending icon demonstrates to the user that the numeric value of the score icon is increasing and that the scale indicator icon is also moving toward the top of the scale. This presents information quickly without the user having to watch the user interface over time.

Figure 8B:
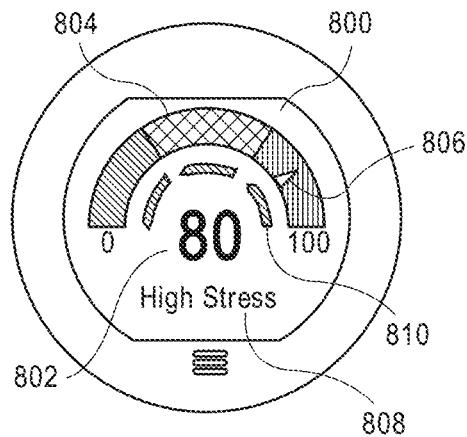

FIG. 8B shows a second exemplary user interface. In this exemplary user interface, the score icon, the scale icon, the scale indicator icon, and the diagnostic icon are the same as those shown in FIG. 8A. However, in FIG. 8B, the trending icon is shown as a series of three bar arrows pointed toward a decreasing of the scale. The trending icon demonstrates to the user that the numeric value of the score icon is decreasing and that the scale indicator icon is also moving toward the bottom of the scale. As in FIG. 8A, this presents information quickly without the user having to watch the user interface over time.

Figure 8C:
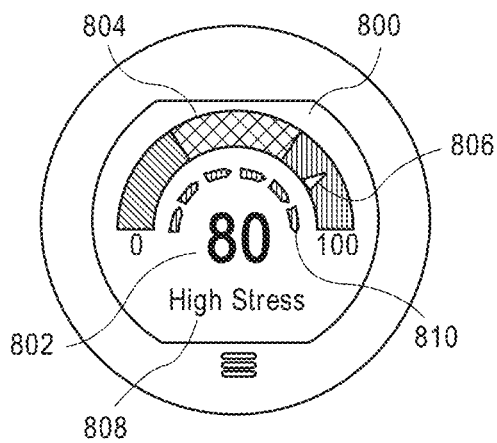
Figure 8D:
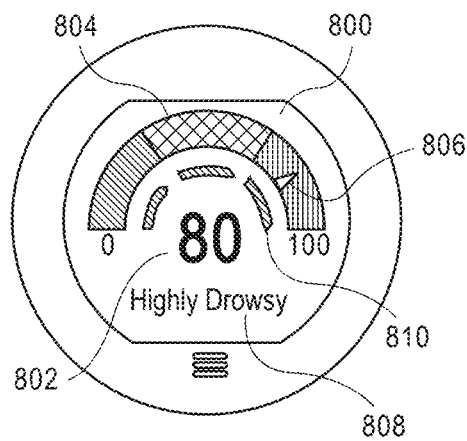

FIG. 8C shows a third exemplary user interface. Like FIG. 8B, the user interface in FIG. 8C is identical to the user interface in FIG. 8A but for the trending icon. In FIG. 8C, the trending icon shows additional bar arrows indicative of an increased trend. For example, six red bars may be presented under the scale icon to illustrate that the user's determined stress level is increasing at a faster pace. In some embodiments, the trending icon may also illustrate movement, increase in size, or perform other visual changes to indicate the trend to the user. In some embodiments, a similar FIG. 8D shows a fourth exemplary user interface. While FIGS. 8A-8C showed a user interface related to stress, FIG. 8D shows another embodiment of a user interface related to drowsiness. It should be appreciated that the various icons and other graphics shown may be used to provide information to any sort of measurement described herein. In this exemplary user interface, the scale indicator icon, shown as an arrow, points to a certain portion of the scale icon (which may be colored red, for example). The location of the scale indicator icon is indicative that the user's determined drowsiness level is high. Additionally, the score icon is shown as a large numeric '80' so as to indicate that the user's determined drowsiness level is 80 within a range of 0 to 100. A diagnostic icon is shown as the text "Highly Drowsy" is presented under the score icon. The diagnostic icon shows the user that the other values presented on the user interface are related to drowsiness (as opposed to another mental state such as stress). Finally, the trending icon is shown as a series of three bar arrows pointed toward an increasing of the scale. The trending icon demonstrates to the user that the numeric value of the score icon is increasing and that the scale indicator icon is also moving toward the top of the scale. This presents information quickly without the user having to watch the user interface over time.

Figure 8E:
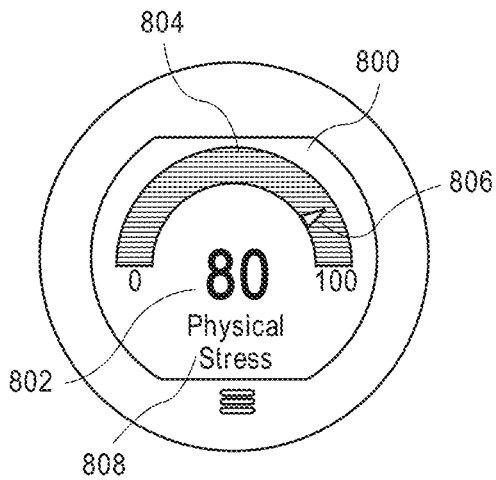

FIG. 8E shows a fifth exemplary user interface. In this embodiment, the diagnostic icon provides an explanation for the score icon, indicative of the reason for the elevated number (in this example). In this example, the entire scale icon is shown as a unitary scale (not broken into zones and may be shown in another color not on the spectrum of red to green, such as blue). The unitary scale is indicative that the normal scale icon is inapplicable to the current situation for some reason. In this example, it is indicative that the user is engaged in a physical activity and a determined high stress level may be due in part or entirely to the current physical activity in which the user is engaging. The diagnostic icon further explains this by showing "Physical Stress" or some other diagnostic explanation. In other embodiments, the user interface may show fewer of the icons so as to indicate that the current situation, namely the physical stress in this example, does not fit within the traditional scale of readings. For example, the user interface may only indicate that there is physical stress, such that the reading or determination is not reliable.

Figure 9:
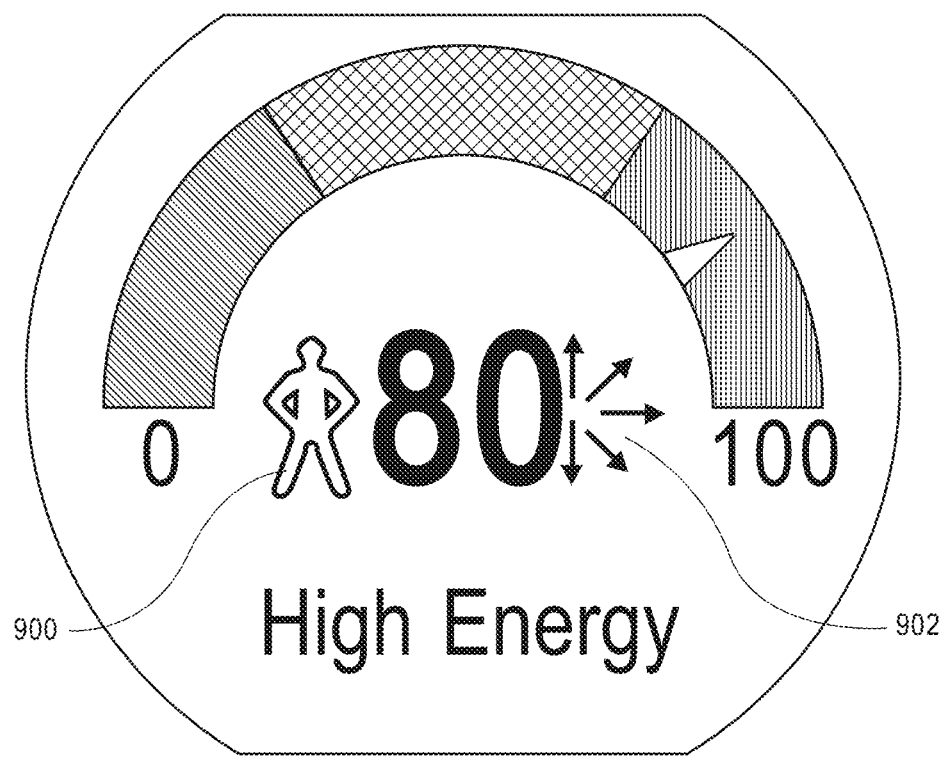
FIGS. 9-12 show an embodiment of the of graphical user interfaces related to a detected energy level.

FIG. 9 shows an example user interface displayed on display 104 of mobile electronic device 100 in accordance with embodiments of the invention. A body energy indicator 900 displays body energy level and status to the user. A current energy level 902 displays current energy level to the user in text (e.g., "High Level" for high level of energy). The energy level may include a numeric energy level displays current energy level to the user as a portion of 100 (e.g., "80" for 80/100 or 80 percent total energy level). The energy level may include a trending indicator of energy level is displayed as an arrow of appropriate color and in appropriate direction to indicate the trend of energy (e.g., accumulating/replenishing or consuming/discharging). Arrows may be of any appropriate or desired color, such as shades of red, orange, yellow, or green.

Figure 10:
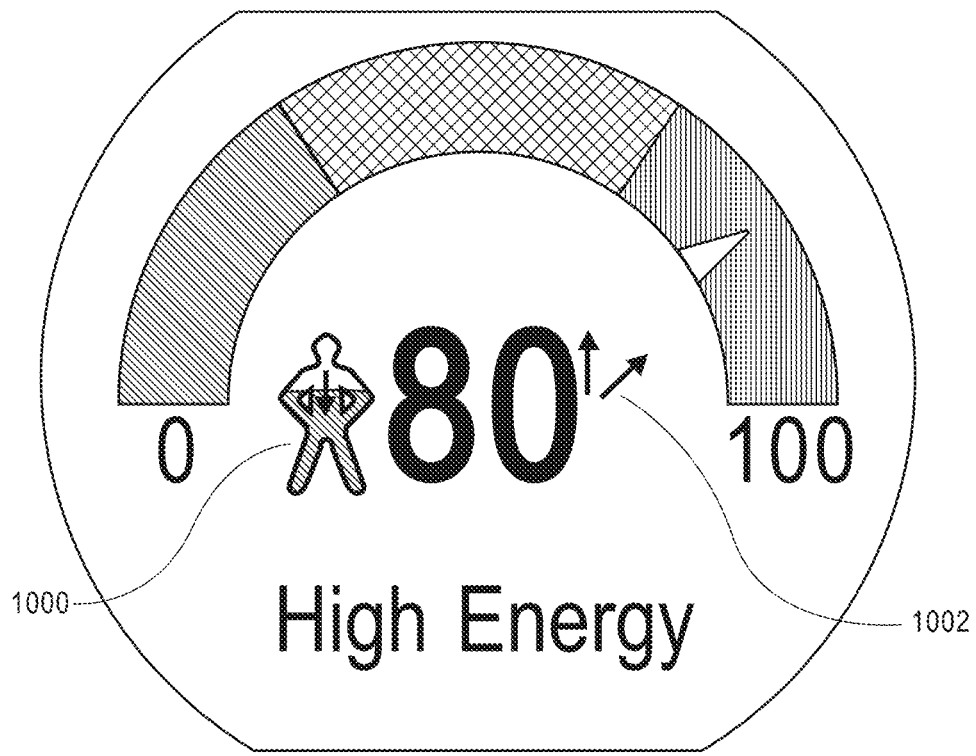

FIG. 10 shows an example user interface displayed on display 104 of mobile electronic device 100 in accordance with embodiments of the invention. Although the appearance is similar to the user interface shown in FIG. 9, the exemplary user interface of FIG. 10 illustrates an example embodiment of integration of both the stress monitoring and body energy level tracking functions. In addition to the arch-shape gauge shown before in user interface 500, the body energy indicator 1002 also indicates trending in body energy level graphically. In FIG. 10, an indication is presented to the user that the user is in a discharging state. Body energy indicator 1002 is approximately 80% filled with green to illustrate the current approximate energy level (e.g., 80 out of 100), and there is a red downward pointing arrow to indicate that energy is discharging as the trend of change in current body energy level. In the discharging state, a red or orange upward pointing arrow may be displayed for the trending indicator of stress level to indicate ongoing stress when instantaneous response is detected.

Figure 11:
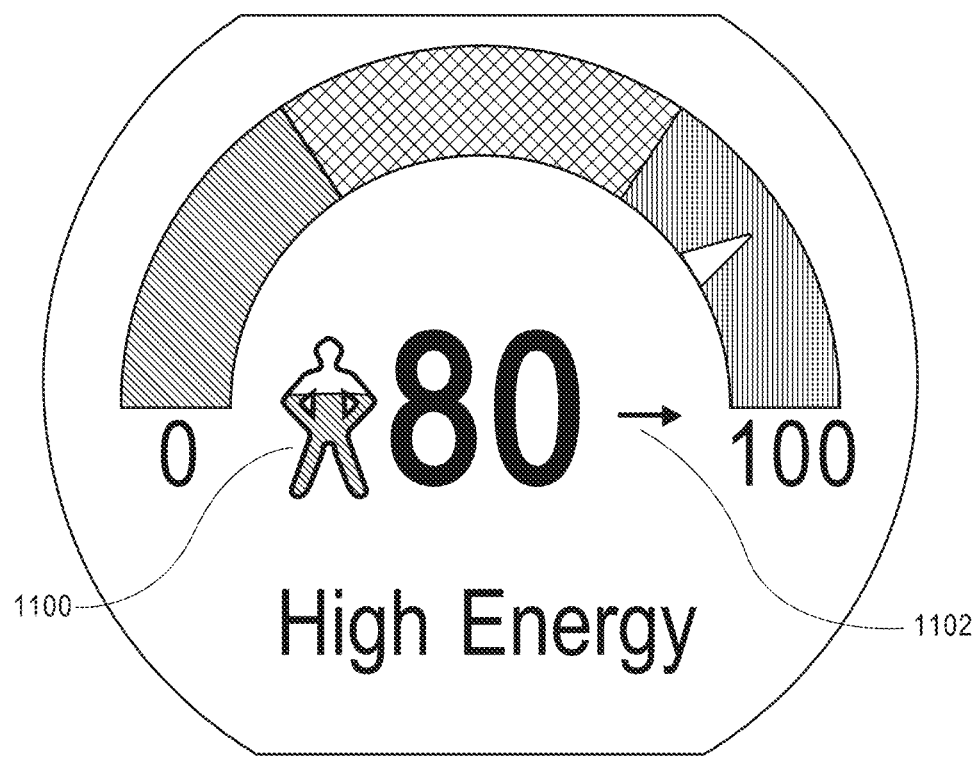

FIG. 11 shows an example user interface displayed on display 104 of mobile electronic device 100 in accordance with embodiments of the invention. The exemplary user interface indicates that the user is in a neutral state (e.g., neither discharging nor accumulating energy). In this example body energy indicator 1100 is partially filled (in this exemplary case, approximately 80% filled) to illustrate the current approximate energy level (e.g., 80 out of 100), but there is no arrow to indicate discharge or accumulation of energy. In the neutral state, no trending indicator may display or a horizontal arrow may be displayed for the trending indicator of stress level when instantaneous response is detected.

Figure 12:
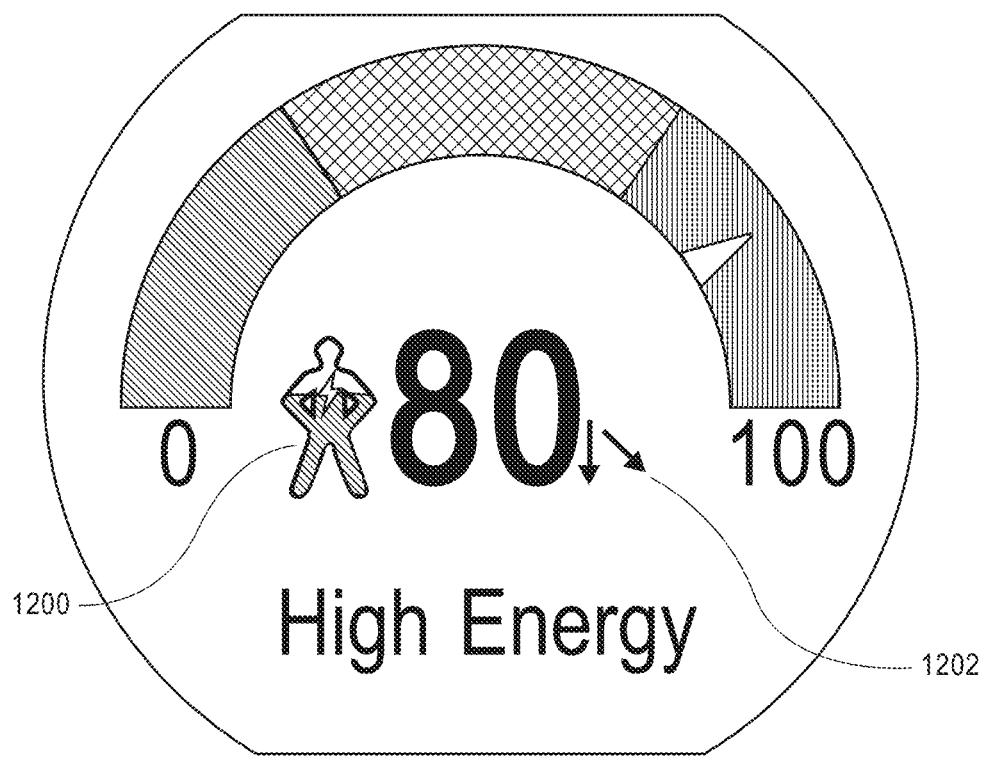

FIG. 12 shows an example user interface displayed on display 104 of mobile electronic device 100 in accordance with embodiments of the invention. This exemplary user interface indicates that the user is in a recharging state. A body energy indicator 802 is approximately 80% filled with green to illustrate the current approximate energy level (e.g., 80 out of 100), and there is a yellow lightning bolt to indicate that energy is recharging. The illustrated lightning bolt can also be replaced by other indicators that imply an increase (e.g., an upward arrow) and may be presented in a highly visible color such as yellow. In the recharging state, a downward pointing arrow in shades of green may be displayed for a stress level trending indicator 804 to indicate recovery when instantaneous response is detected and within the range of 0 to +100.

Example Blood Pressure Detection System

In embodiments of the invention, the mobile electronic device 100 may utilize blood pressure readings in addition to the above-discussed heartrate readings in determining one or more of the mental states, alerts, and other functions described herein. The mobile electronic device 100 of these embodiments may include a blood pressure sensor (as shown in FIG. 2) which is operable to sample a user's electrocardiogram/photoplethysmogram (ECG/PPG) signals to measure a blood pressure for the user. Normalized BP may be calculated by the processor 210 and displayed based on BP measurements analyzed in light of other sensed or otherwise available biometric parameters, such as motion, HR, HRV, and so on. When the mobile electronic device 100 samples (either directly through an internal blood pressure sensor 226 or an external blood pressure sensor) the user's ECG/PPG, it may instruct the user to sit in an upright position at rest. The user may also be directed to press the user's finger in a certain spot on the mobile electronic device 100 to facilitate collection of a sample. For example, the display 104 may present an arrow pointing toward a particular part of the bezel at which the user should place a finger from the other hand. The point may be determined by the processor 210 of the mobile electronic device 100 based on sensed data, such as the fidelity of the ECG signal. Poor ECG signal fidelity may result in the interface directing the user to change the contact point as needed.

The mobile electronic device 100 may automatically determine whether the user is wearing the mobile electronic device 100 on the right or left hand and adjust accordingly to correctly orientate the ECG signal prior to processing. In embodiments, the mobile electronic device 100 may prompt the user to select which hand the mobile electronic device 100 is being worn on manually. Additionally or alternatively, the mobile electronic device 100 may use the accelerometer 224 in conjunction with the user holding the user's arm in a pre-determined position. For example, the user may hold the user's arm out in front of the user's body with the face of the device orientated toward the user's face. The mobile electronic device 100 may then be able to identify whether it is being worn on the right or left hand via acceleration signals from an inertial sensor (e.g., accelerometer 224, gyroscope, etc.). Additionally or alternatively, the mobile electronic device 100 may be able to identify whether it is worn on the right or left hand based on inertial data alone or in conjunction with other sensed data. Additionally or alternatively, the mobile electronic device 100 may recognize key components of the ECG signal, such as whether the QRS complex is orientated correctly or is inverted, and use software algorithms to identify whether the mobile electronic device 100 is being worn on the right or left hand.

Figure 13C:
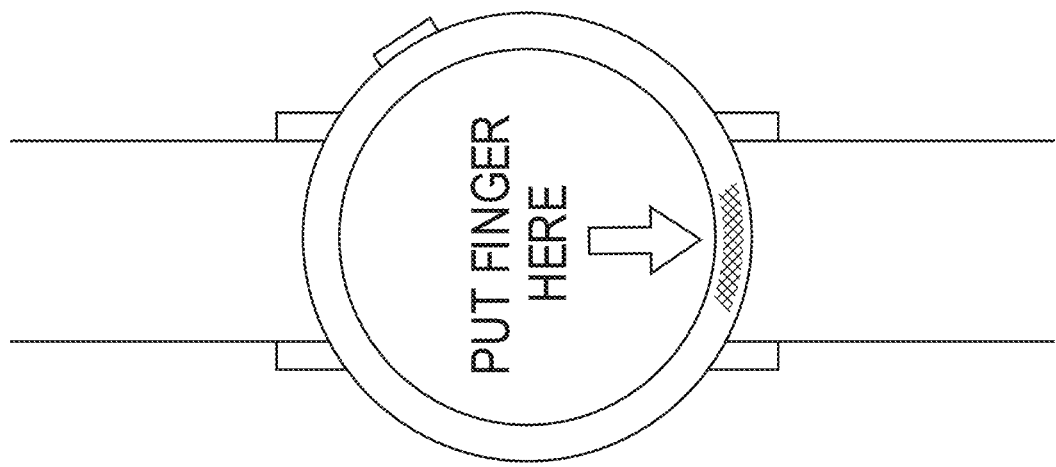
FIGS. 13A-13C show embodiments of a user interface directing a user to perform a blood pressure reading.
Figure 13B:
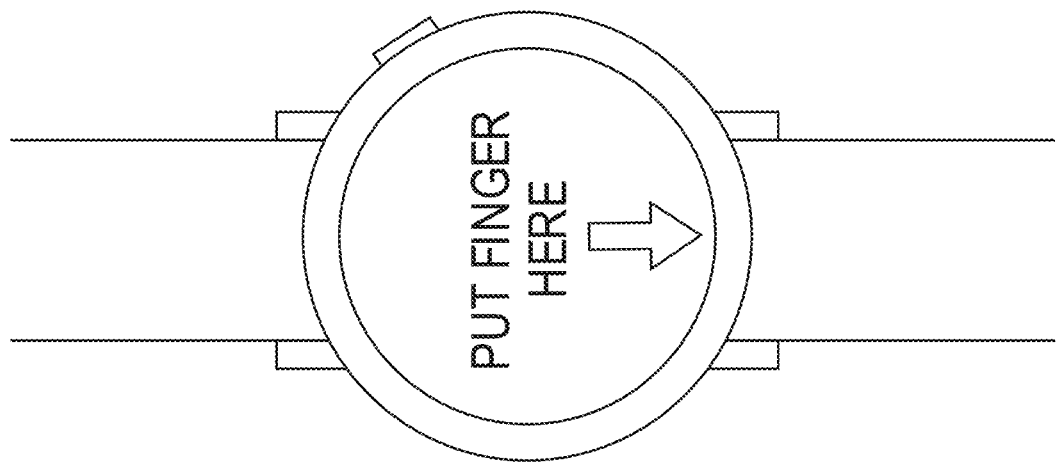
Figure 13A:
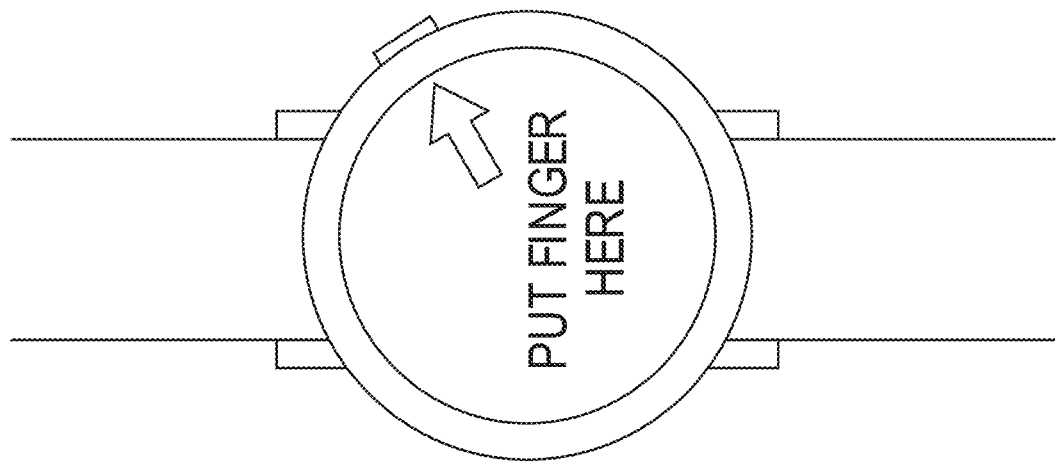

FIGS. 13A-13C show example user interfaces displayed on display 104 of mobile electronic device 100 (in this example, a smartwatch) in accordance with embodiments of the invention. In FIG. 13A, the user is directed to place the user's finger on the button 106 on the top-right portion of the bezel. In FIG. 13B, the user is directed to put the user's finger on a bezel of the housing 102. In these embodiments, the entire bezel may be an ECG contact location. In FIG. 13C, the user is directed to put the user's finger on a certain location of the bezel (as illustrated, the lowest point of the bezel). In these embodiments, the ECG contact and the rest of the bezel is not part of the lead.

The processor 210 may require anywhere from one second to 120 seconds to obtain a sample depending on the strength and quality of the ECG signal. During sample collection, the user may be presented with a graphical display of either the actual ECG signal or a simulated ECG signal, a blinking light, a countdown timer, a progress bar, educational information (e.g., definition of systolic pressure, what a "good" BP value range is, general wellness tips including tips to reduce blood pressure, etc.), or any other suitable information or graphical display. At the beginning and/or end of the sample collection, the mobile electronic device 100 may alert the user that the sample has started and/or finished (e.g., beeps, haptic feedback such as vibration). Other auditory, visual, or haptic feedback may be provided as desired. For example, once the mobile electronic device 100 has acquired the ECG signal, the mobile electronic device 100 may vibrate the user's pulse or at any other interval to indicate that the measurement is in progress. The mobile electronic device 100 may also produce various tactile feedback, such as feedback that mimics the experience of a traditional blood pressure cuff.

Figure 14:
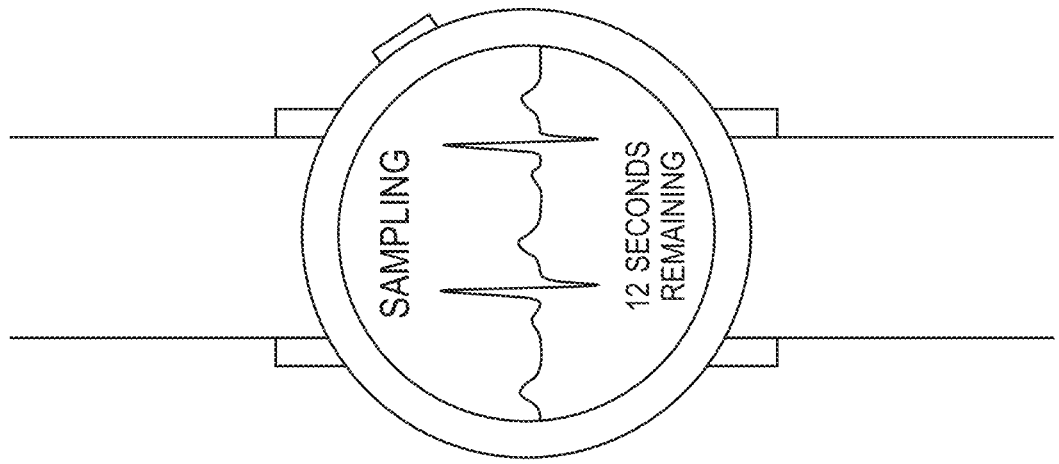
FIG. 14 shows an embodiment of user interface a sampling blood pressure sensor.

FIG. 14 shows an example user interface presented on display 104 of mobile electronic device 100 in accordance with embodiments of the invention. The example user interface demonstrates that a reading is taking place. In this exemplary user interface, the user is shown the word "Sampling" to indicate that a sample is being taken at the moment, a graphical representation of an ECG signal (either actual or simulated), and a countdown of how much longer the process of sample collection will take ("12 seconds remaining"). This user interface is merely exemplary, and embodiments of the invention may show more or less information during the sampling.

In embodiments of the invention, the mobile electronic device 100 may pair with another device, such as a user's smartphone, to sync data or otherwise allow the user to interact with the mobile electronic device 100 or review information and data provided. An application (app) may be used to provide this user interface. The mobile electronic device 100 may sync automatically on a certain interval, automatically after a certain amount of data is available to sync, upon request by the user, or upon any other desired event or threshold. The mobile electronic device 100 and/or its accompanying app may generate smart reminders for the user to check the user's blood pressure. These may be based on a set time interval or upon other data (e.g., if the user's HR is too high, the smart reminder may be delayed; if a user has not been at rest or dropped below a certain threshold of accelerometer data, the smart reminder may be delayed). The smart reminder may also be turned off completely or set manually by the user as desired. Additionally or alternatively, push notifications may be used to remind the user to take the user's BP or to coach a user to adjust behavior. For example, a user may be notified in the morning that he or she should drink a glass of water or take blood pressure medication.

Figure 15:
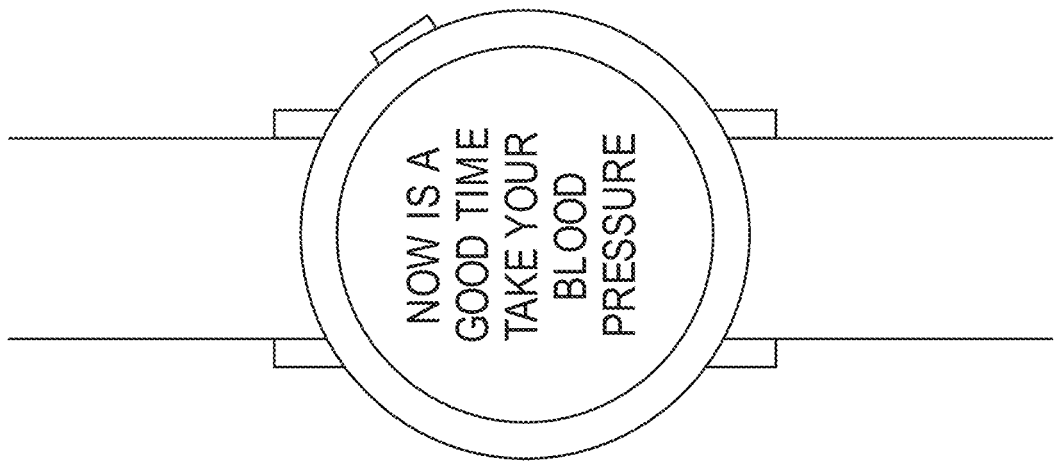
FIG. 15 shows an embodiment of a user interface reminding the user to sample blood pressure.

FIG. 15 shows an example user interface presented on display 104 of mobile electronic device 100 in accordance with embodiments of the invention and a flow chart related to measurement prompts. The user interface shows a reminder, notification, or other message indicative for the user to take a blood pressure reading. For example, the text shown in FIG. 15 states "Now is a good time to take your blood pressure," to prompt the user to participate in a measurement. As mentioned above, reminders may be shown at certain times or at set intervals. At the time that a measurement would normally be requested, the mobile electronic device 100 may determine if there is recent high activity. If so, the processor 210 may wait to prompt for a pre-set number of minutes (e.g., 15 minutes) before the next check. If there was not recent high activity, the user may be prompted for measurement, as this may be a good time for the user.

Rewards, achievements, or other encouragements may also be shown to the user to provide the user's progress or successful measurements and collection of data. For example, the mobile electronic device 100 may provide on display 104 streak tracking (e.g., keeping track of how many times a user has hit a particular target, such as a certain number of consecutive BP measurements within a desired range or a certain number of consecutive days of taking BP measurements). The mobile electronic device 100 may congratulate the user or reward the user, for example, sending notifications to connected third parties, such as friends or relatives, which may prompt them to congratulate or otherwise recognize the user.

Figure 16:
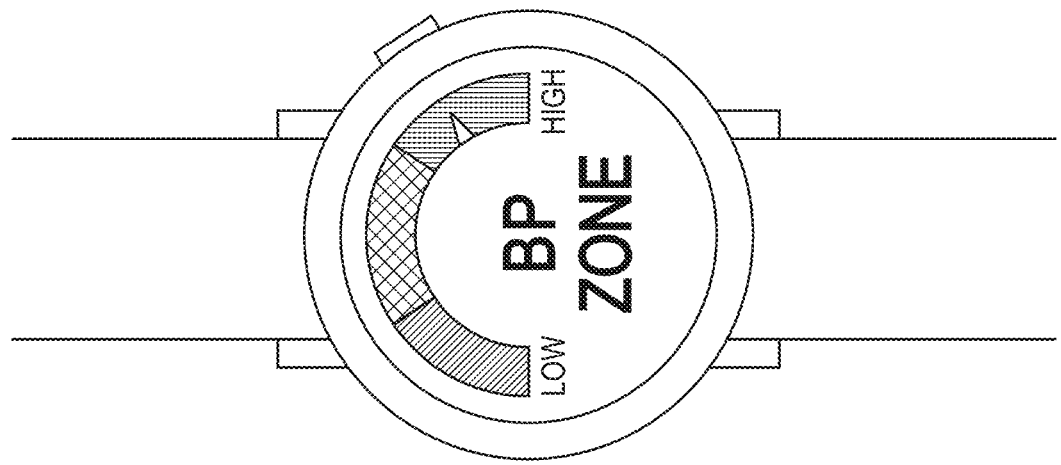
FIG. 16 shows an embodiment of a user interface displaying the results of a blood pressure reading.

FIG. 16 shows an example user interface on a mobile electronic device 100 in accordance with embodiments of the invention. The user interface shows a result of a blood pressure measurement. A blood pressure scale icon, similar to the scale icon discussed above, is shown for the user, with a scale indicator icon thereon. Other indicators such as a score indicator, a trending indicator, and the like may also be displayed to the user.

Figure 17C:
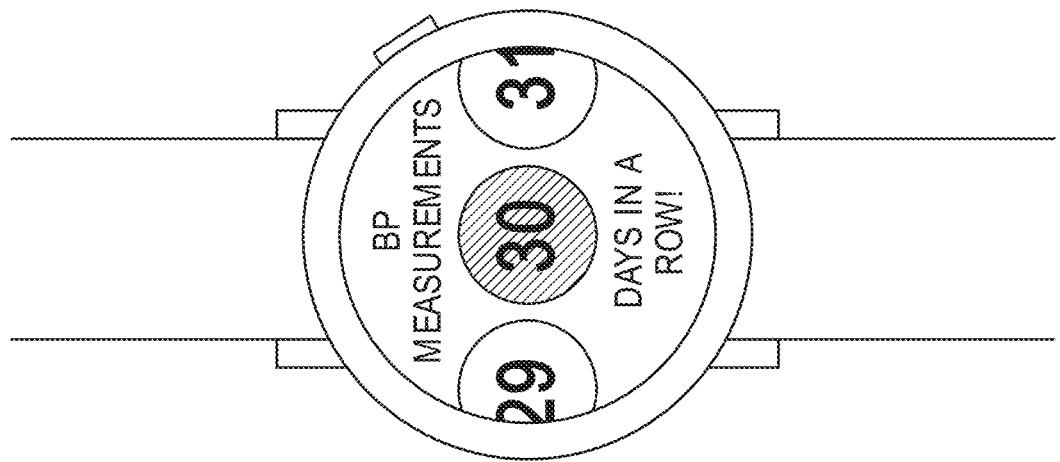
FIGS. 17A-17C show embodiments of a user interface rewarding the user for taking blood pressure samples.
Figure 17B:
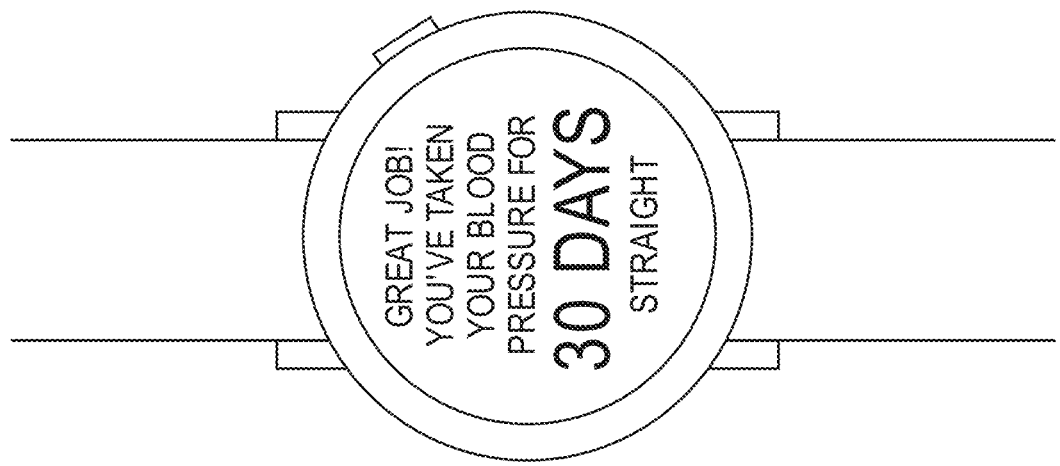
Figure 17A:
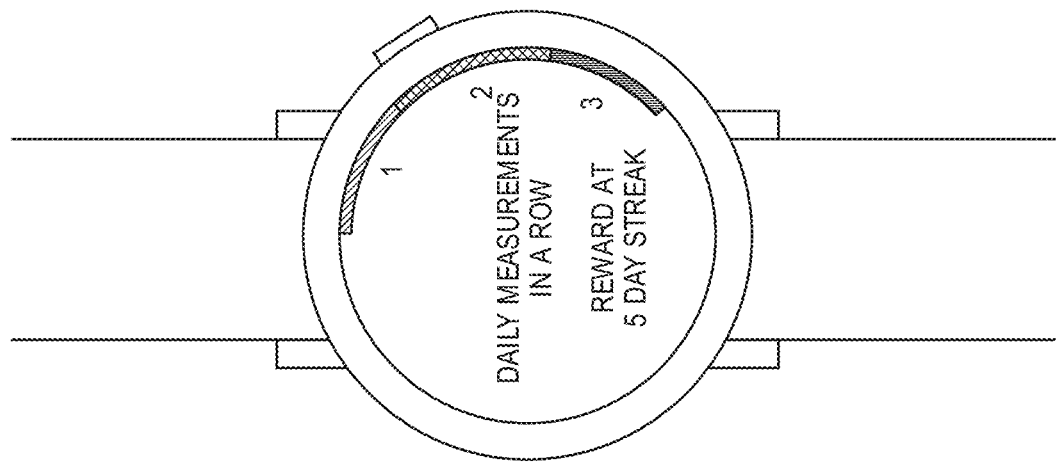

FIG. 17 shows another example user interface presented on display 104 of mobile electronic device 100 in accordance with embodiments of the invention. FIG. 17A presents the number of daily measurements that were successfully captured graphically along the side of the interface. This example shows that there have been three daily measurements taken successfully. FIG. 17A also shows that a reward will be earned after a five-day streak. FIG. 17B shows a congratulatory message to the user after successfully taking BP measurements for thirty days in a row. FIG. 17C shows a graphical representation that BP measurements have been taken for thirty days in a row.

On display 104 of the mobile electronic device 100 and/or its accompanying app and/or paired device, the user may view their blood pressure and compare it to the BP measurements of similar demographics (e.g., people of the same age, gender, or height). The user may also view a correlation of their BP to other captured biometric data, such as calories consumed, calories burned, sleep quantity, sleep quality, mood, stress level, or any other suitable data or metric. The mobile electronic device 100 and/or its accompanying app and/or paired device may link to a user's third-party applications that track related information (e.g., MYFITNESSPAL, APPLE health kit app, and so on). Third-party applications may also be created, such as those using GARMIN ConnectIQ, to allow these other applications to make use of this data and feature set. A user may wish to share the user's ECG data. This data may be shared directly from the mobile electronic device 100 to selected recipients (such as the user's physician) via text or email, a webservice such as GARMIN Connect, or via any other suitable means.

The display 104 of mobile electronic device 100 and/or its accompanying app and/or paired device may present BP zones using color-coding or labels. For example, a color spectrum of gray, blue, green, orange, and red may be used to indicate very low, low, average, high, and very high level of BP or normalized BP, respectively. BP readings may also be categorized into groups based on activity level or other available data (e.g., HR). For example, if a user's resting HR is 60, all BP measurements taken when the user's HR is in the range of 55-66 may be grouped into an "at rest" category. Similarly, stress level and/or stress score or other biometric data-based or calendar-based information may be used to categorize BP measurements.

Conclusion

Although systems and methods for have been disclosed in terms of specific structural features and acts, it is to be understood that the appended claims are not to be limited to the specific features and acts described. Rather, the specific features and acts are disclosed as exemplary forms of implementing the claimed devices and techniques.

The invention claimed is:

1. A mobile electronic device operable to detect and display a mental state of a user, the mobile electronic device comprising:
    a heartrate sensor operable to provide a heartbeat signal indicative of a heartbeat of the user;
    a processor operable to:
        acquire a beat-to-beat interval based upon the heartbeat signal;
        filter the detected beat-to-beat interval to determine a beat-to-beat interval curve;
        perform a Fourier analysis on the beat-to-beat interval curve to determine a high-frequency power of the beat-to-beat interval curve and a low-frequency power of the beat-to-beat interval curve; and
        determine a drowsiness level of the user based at least in part upon the beat-to-beat interval; and
    a display operable to display an indication of the drowsiness level;
    wherein the low-frequency power being under a low-frequency power threshold and upon the high-frequency power being above a high-frequency power threshold is indicative that the mental state of the user is drowsy; and
    wherein the low-frequency power being above a low-frequency power threshold and upon the high frequency power being under a high-frequency power threshold is indicative that mental state of the user is stressed.

2. The mobile electronic device of claim 1, wherein the display is further operable to display a trending icon indicative of a trend of the drowsiness level.

3. The mobile electronic device of claim 1, further comprising:
    an accelerometer operable to detect movement by the user,
    wherein the processor is further operable to determine the drowsiness level of the user utilizing at least the detected movement and the beat-to-beat interval.

4. The mobile electronic device of claim 1, further comprising:
    a location determining component operable to determine a speed of the user,
    wherein the processor is further operable to:
        determine that the user is driving based upon the speed; and
        instruct a remedial action upon the determined drowsiness level being above a threshold.

5. The mobile electronic device of claim 1, further comprising:
    a communication element operable to send information indicative of the determined drowsiness level to an external computing device.

6. The mobile electronic device of claim 1, further comprising:
    a blood pressure sensor operable to provide a blood pressure indication indicative of a blood pressure of the user,
    wherein the processor is further operable to determine the mental state of the user based at least in part of the blood pressure indication.

7. The mobile electronic device of claim 1, wherein the processor is further operable to:
    collect a first plurality of readings during awake periods and a second plurality of readings during sleep periods;
    analyze the first plurality to determine an average awake value for the user;
    analyze the second plurality to determine an average sleep value for the user; and
    determine the low-frequency power threshold and the high-frequency power threshold based at least in part upon the average awake value and the average sleep value.

8. A mobile electronic device operable to detect and display a mental state of a user, the mobile electronic device comprising:
    a heartrate sensor operable to provide a heartbeat signal indicative of a heartbeat of the user;
    a processor operable to:
        acquire a beat-to-beat interval based upon the heartbeat signal; determine a mental state of the user based at least in part upon the beat-to-beat interval at a time TI;
        determine a mental state of the user based at least in part upon the beat-to-beat interval at a time T2,
        wherein the time T2 is distinct from and later than the time T1;
        determine a mental state trend based at least in part on the mental state at time T1 and the mental state at time T2; and
    a display operable to display:
        a diagnosis icon indicative of the mental state at time T2; and
        a trending icon indicative of the mental state trend;

wherein the processor, at both time T1 and time T2, is further operable to:
  filter the detected beat-to-beat interval to determine a beat-to-beat interval curve;
  perform a Fourier analysis on the beat-to-beat interval curve to determine a high-frequency power of the beat-to-beat interval curve and a low-frequency power of the beat-to-beat interval curve, and
  determine the mental state of the user further based at least in part on the low-frequency power and the high-frequency power,
wherein the low-frequency power being under a low-frequency power threshold and upon the high-frequency power being above a high-frequency power threshold is indicative that the mental state of the user is drowsy; and
wherein the low-frequency power being above a low-frequency power threshold and upon the high frequency power being under a high-frequency power threshold is indicative that mental state of the user is stressed.

9. The mobile electronic device of claim 8, further comprising:
  a watch housing securing the heartrate sensor, the processor, and the display, and
  a watch band secured to the watch housing and operable to secure the watch housing to a wrist of the user.

10. The mobile electronic device of claim 8, wherein the trending icon is indicative of a magnitude of the trend.

\* \* \* \* \*